(12) United States Patent
Hassan et al.

(10) Patent No.: US 8,308,673 B2
(45) Date of Patent: Nov. 13, 2012

(54) METHODS AND DEVICES FOR REMOVAL OF A MEDICAL AGENT FROM A PHYSIOLOGICAL EFFERENT FLUID COLLECTION SITE

(75) Inventors: Ali Hassan, Mountain View, CA (US); Lester John Lloyd, Orinda, CA (US); Michael Orth, Los Gatos, CA (US); Mark Yang, Los Gatos, CA (US); Binh Luong, Los Gatos, CA (US); Brian K. Courtney, Toronto (CA); Peter J. Fitzgerald, Portola Valley, CA (US)

(73) Assignee: Catharos Medical Systems, Inc., Campbell, CA (US)

( * ) Notice: Subject to any disclaimer, the term of this patent is extended or adjusted under 35 U.S.C. 154(b) by 811 days.

(21) Appl. No.: 12/138,291

(22) Filed: Jun. 12, 2008

(65) Prior Publication Data

US 2009/0048552 A1    Feb. 19, 2009

Related U.S. Application Data

(60) Provisional application No. 60/934,511, filed on Jun. 13, 2007.

(51) Int. Cl.
*A61M 37/00* (2006.01)
*A61M 1/00* (2006.01)
*A61M 31/00* (2006.01)

(52) U.S. Cl. ............. 604/5.01; 604/4.01; 604/5.04; 604/6.09; 604/6.16; 604/27; 604/28; 604/30; 604/35; 604/500; 604/503; 604/506; 604/507; 604/508

(58) Field of Classification Search ............. 604/4.01, 604/5.01, 6.16, 27, 28, 30, 35, 500, 503, 604/506, 507, 508, 510, 513, 65, 66, 67, 604/104, 118, 119, 174, 181, 246, 264, 32; 422/44; 606/200
See application file for complete search history.

(56) References Cited

U.S. PATENT DOCUMENTS

| | | | |
|---|---|---|---|
| 3,616,272 | A | 10/1971 | Goerg et al. |
| 3,903,895 | A | 9/1975 | Alley et al. |
| 4,103,685 | A | 8/1978 | Lupien et al. |
| 4,652,255 | A | 3/1987 | Martinez |
| 4,666,426 | A | 5/1987 | Aigner |
| 4,753,640 | A | 6/1988 | Nichols et al. |
| 4,792,689 | A | 12/1988 | Peterson |
| 4,939,468 | A | 7/1990 | Takeuchi |

(Continued)

FOREIGN PATENT DOCUMENTS

GB        2350794 A    12/2000

(Continued)

*Primary Examiner* — Tatyana Zalukaeva
*Assistant Examiner* — Adam Marcetich
(74) *Attorney, Agent, or Firm* — Bozicevic, Field & Francis LLP; Bret E. Field

(57) ABSTRACT

Methods and devices for selectively removing an agent from a physiological site, e.g., a physiological efferent fluid collection site, are provided. Aspects of the invention include fluid removal (e.g., aspiration) devices having a fluid removal element and a flow modulator positioned at a distal end of the fluid removal element. The flow modulator is configured to converge intersecting fluid flow paths into the fluid removal element. Also provided are systems and kits for performing the subject methods. The subject invention finds use in a variety of different applications, including the selective removal of both therapeutic and diagnostic agents from a variety of different physiological sites.

26 Claims, 23 Drawing Sheets

U.S. PATENT DOCUMENTS

| | | | |
|---|---|---|---|
| 5,011,488 A * | 4/1991 | Ginsburg | 606/159 |
| 5,113,358 A | 5/1992 | Reber | |
| 5,649,905 A | 7/1997 | Zanger et al. | |
| 5,713,860 A * | 2/1998 | Kaplan et al. | 604/103.01 |
| 5,800,457 A * | 9/1998 | Gelbfish | 606/200 |
| 5,865,802 A * | 2/1999 | Yoon et al. | 604/104 |
| 6,312,407 B1 | 11/2001 | Zadno-Azizi et al. | |
| 6,413,233 B1 | 7/2002 | Sites et al. | |
| 6,524,323 B1 * | 2/2003 | Nash et al. | 606/159 |
| 6,537,247 B2 * | 3/2003 | Shannon | 604/103.05 |
| 6,558,349 B1 * | 5/2003 | Kirkman | 604/104 |
| 6,562,020 B1 | 5/2003 | Constantz et al. | |
| 6,702,834 B1 * | 3/2004 | Boylan et al. | 606/200 |
| 7,211,073 B2 | 5/2007 | Fitzgerald et al. | |
| 7,678,131 B2 * | 3/2010 | Muller | 606/200 |
| 2001/0044591 A1 | 11/2001 | Stevens et al. | |
| 2002/0099254 A1 | 7/2002 | Movahed | |
| 2003/0040736 A1 | 2/2003 | Stevens et al. | |
| 2003/0100917 A1 * | 5/2003 | Boyle et al. | 606/200 |
| 2004/0011740 A1 | 1/2004 | Bernard et al. | |
| 2004/0044302 A1 | 3/2004 | Bernard et al. | |
| 2004/0111111 A1 * | 6/2004 | Lin | 606/200 |
| 2004/0167385 A1 | 8/2004 | Rioux et al. | |
| 2004/0254523 A1 | 12/2004 | Fitzgerald et al. | |
| 2005/0004476 A1 | 1/2005 | Payvar et al. | |
| 2005/0085769 A1 | 4/2005 | MacMahon et al. | |
| 2005/0100937 A1 | 5/2005 | Holmes | |
| 2005/0124969 A1 * | 6/2005 | Fitzgerald et al. | 604/508 |
| 2005/0159770 A1 * | 7/2005 | Divani et al. | 606/200 |
| 2008/0041516 A1 * | 2/2008 | Chiu et al. | 156/173 |
| 2008/0108960 A1 * | 5/2008 | Shapland et al. | 604/321 |

FOREIGN PATENT DOCUMENTS

| | | |
|---|---|---|
| WO | WO02058777 A2 | 8/2002 |
| WO | WO02060511 A2 | 8/2002 |
| WO | W02004083817 | 9/2004 |
| WO | W02006042219 | 4/2006 |
| WO | W02007103279 | 9/2007 |

* cited by examiner

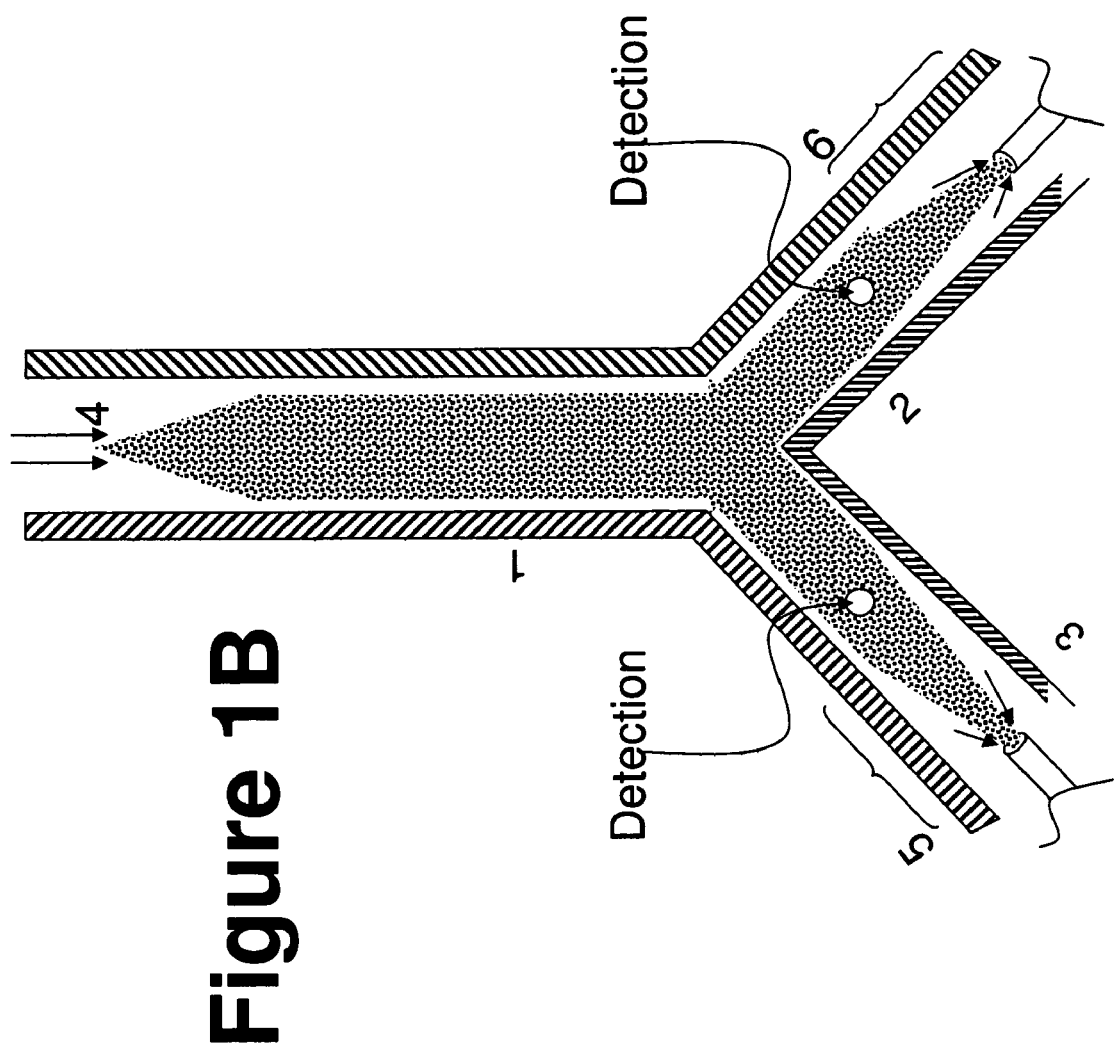

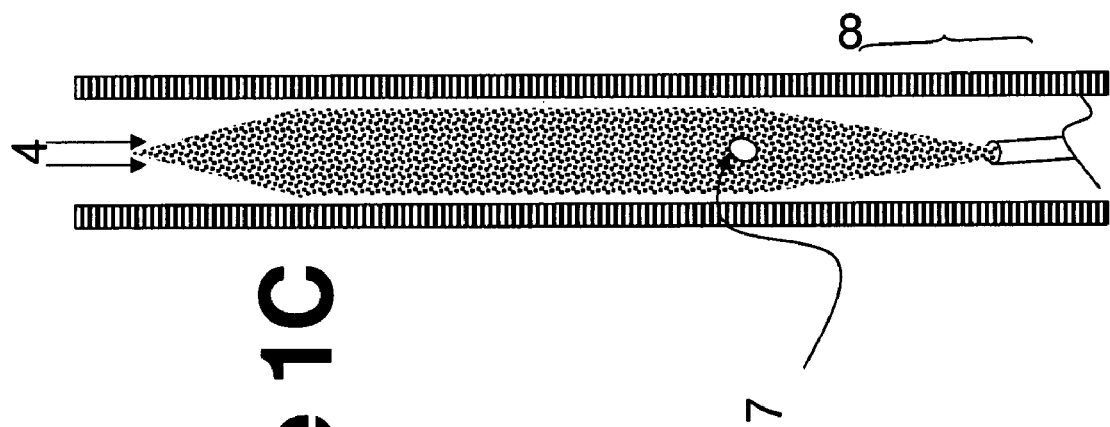

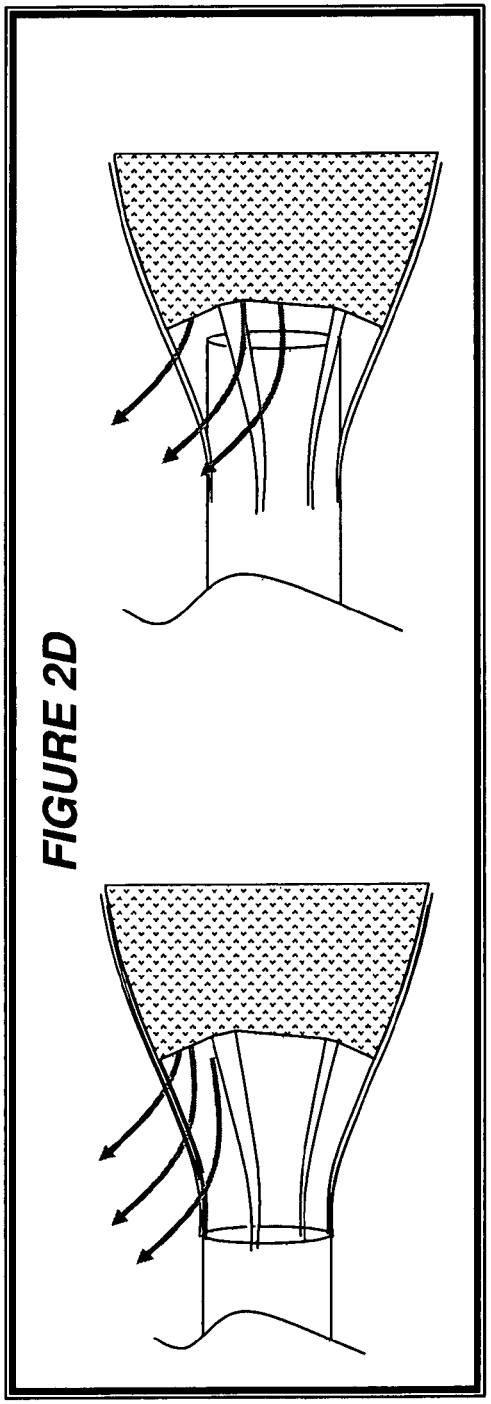
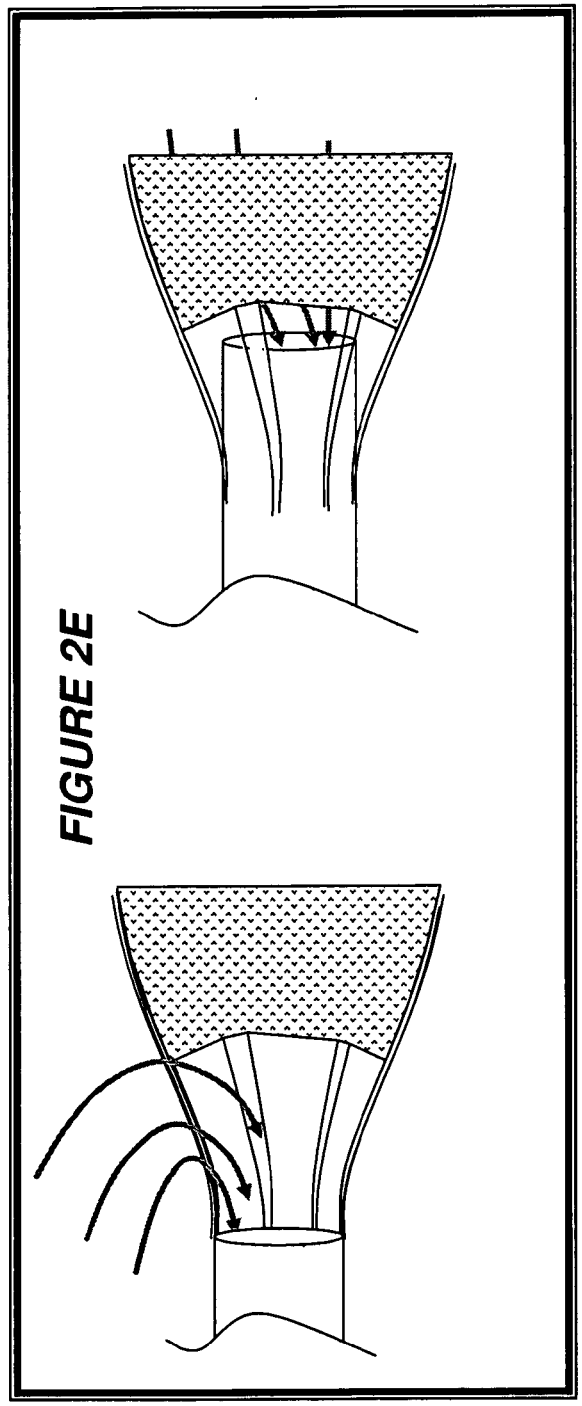
*FIGURE 2D*
*FIGURE 2E*

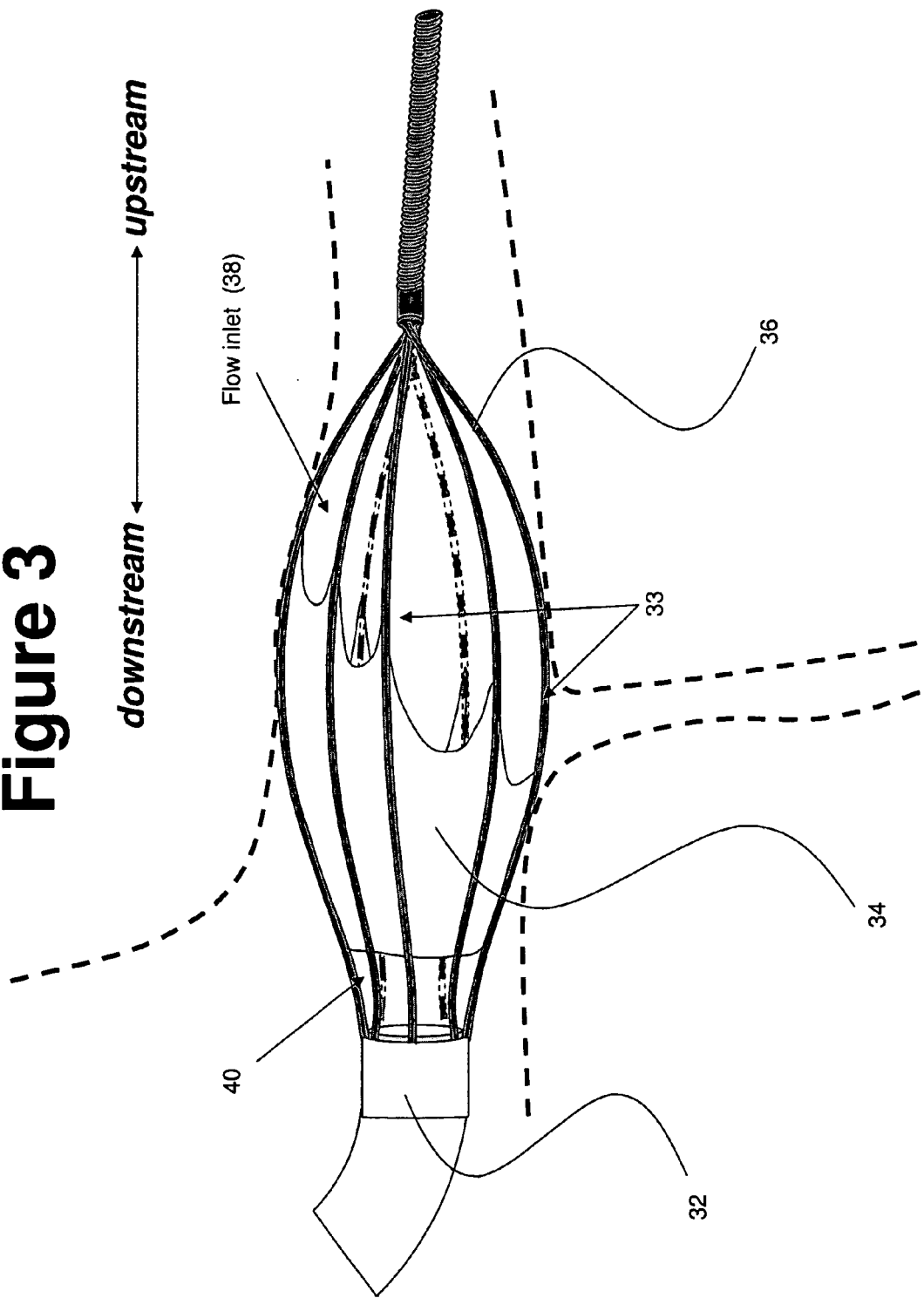

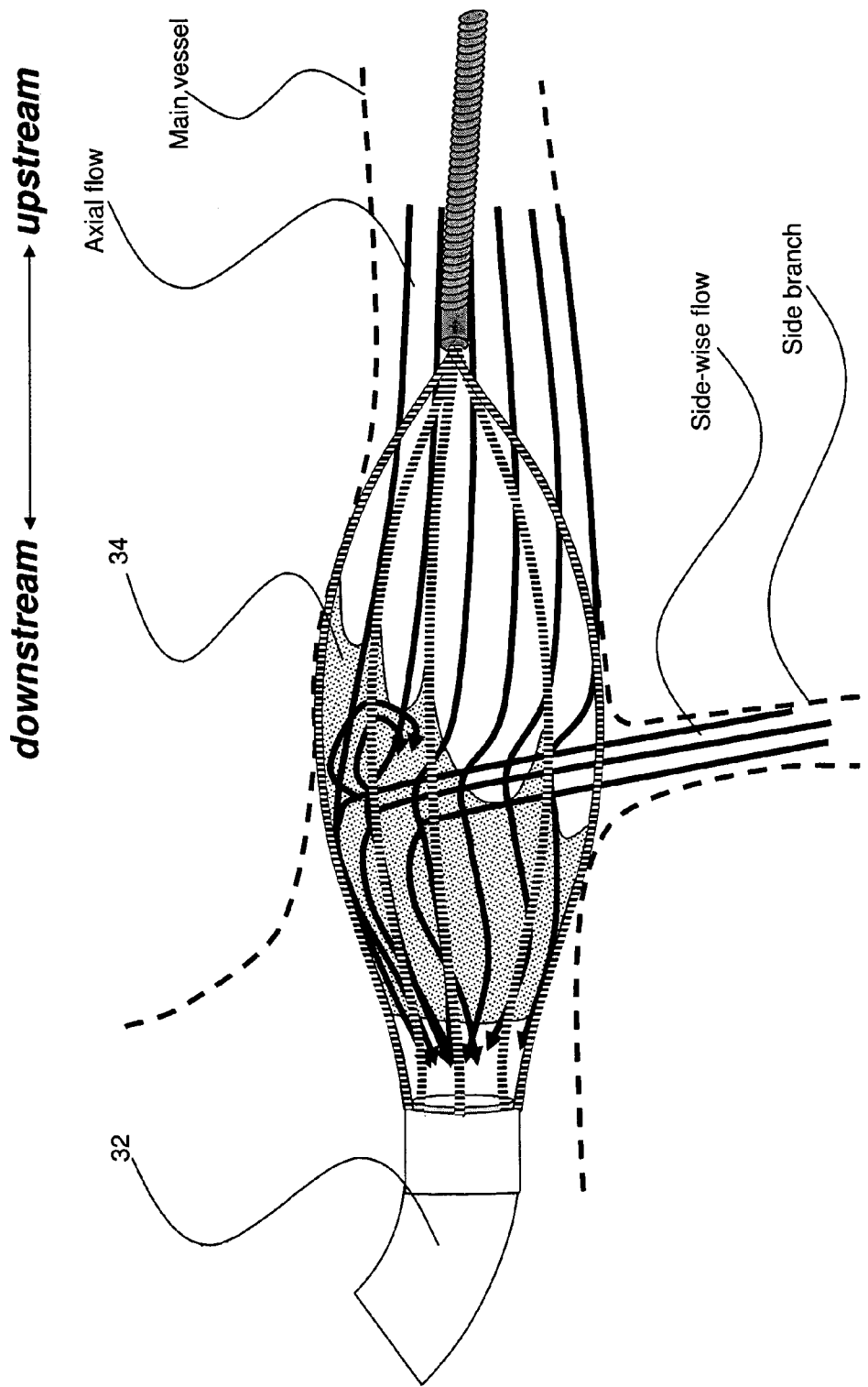

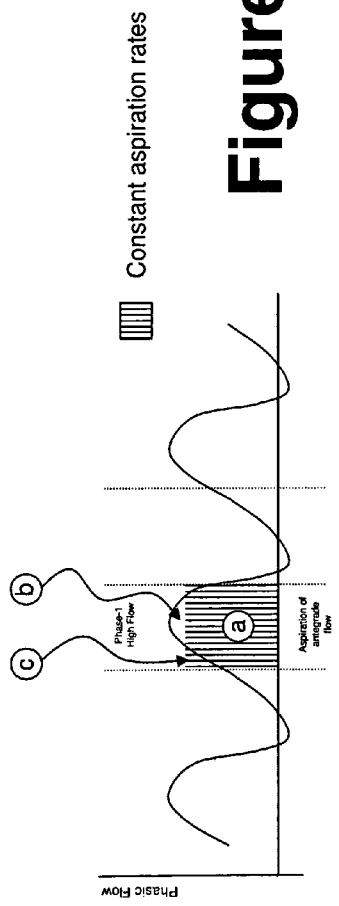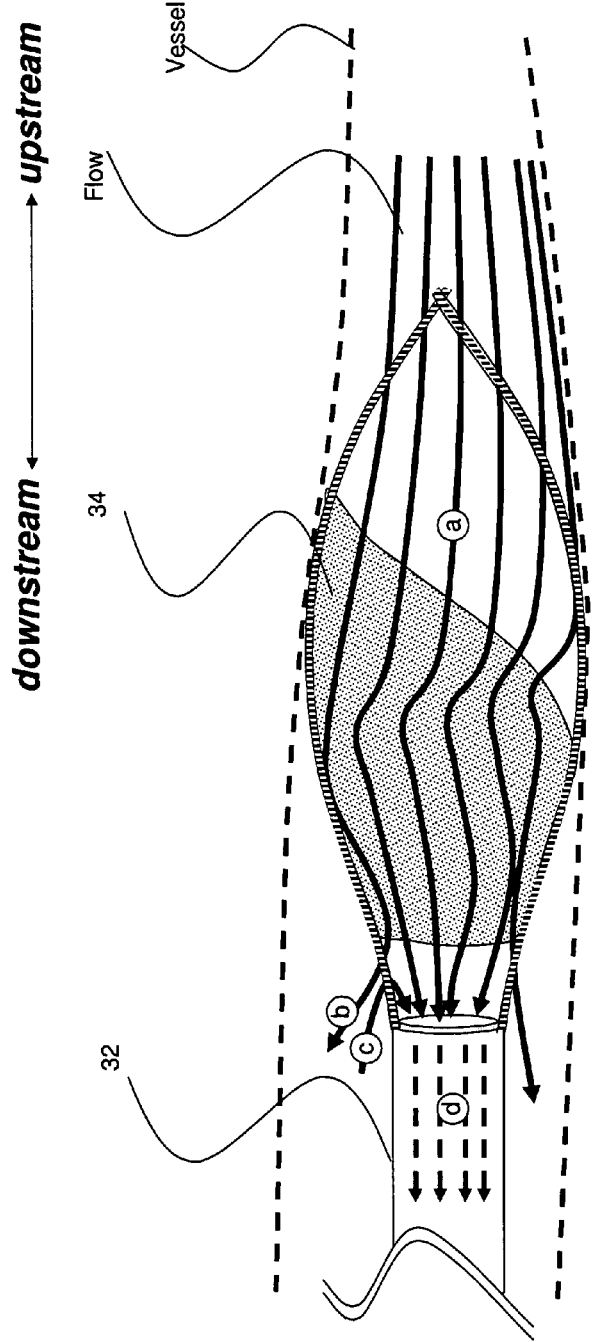
Figure: 4B

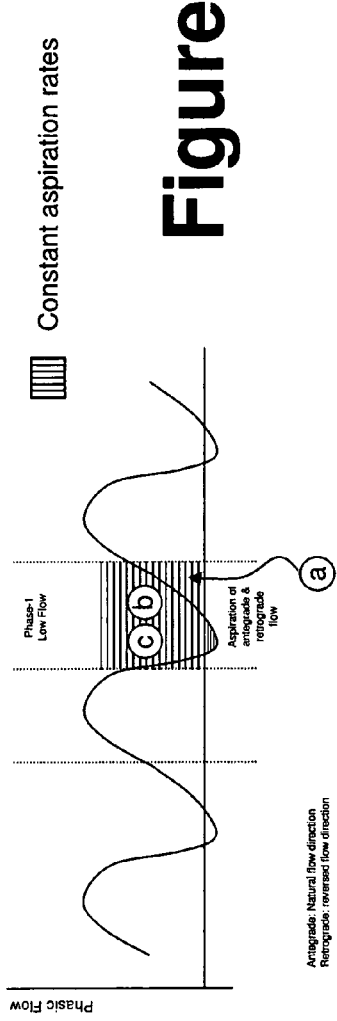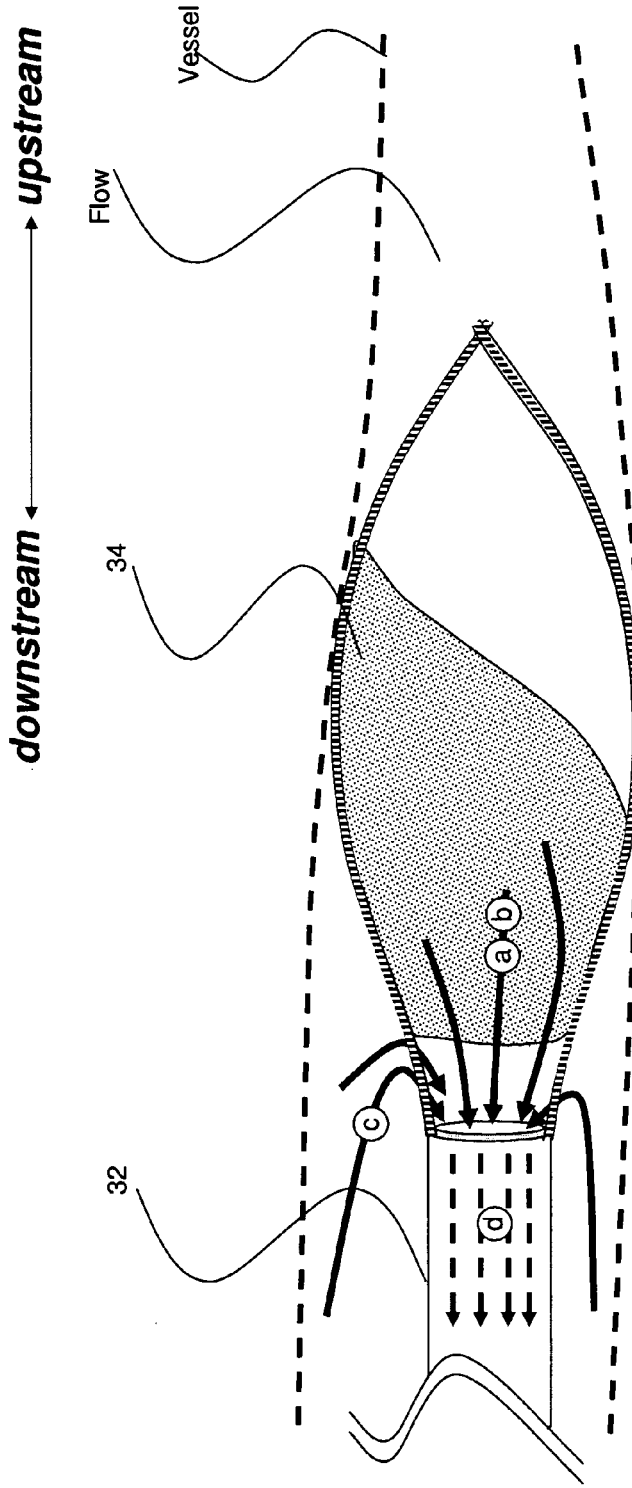
Figure 4C

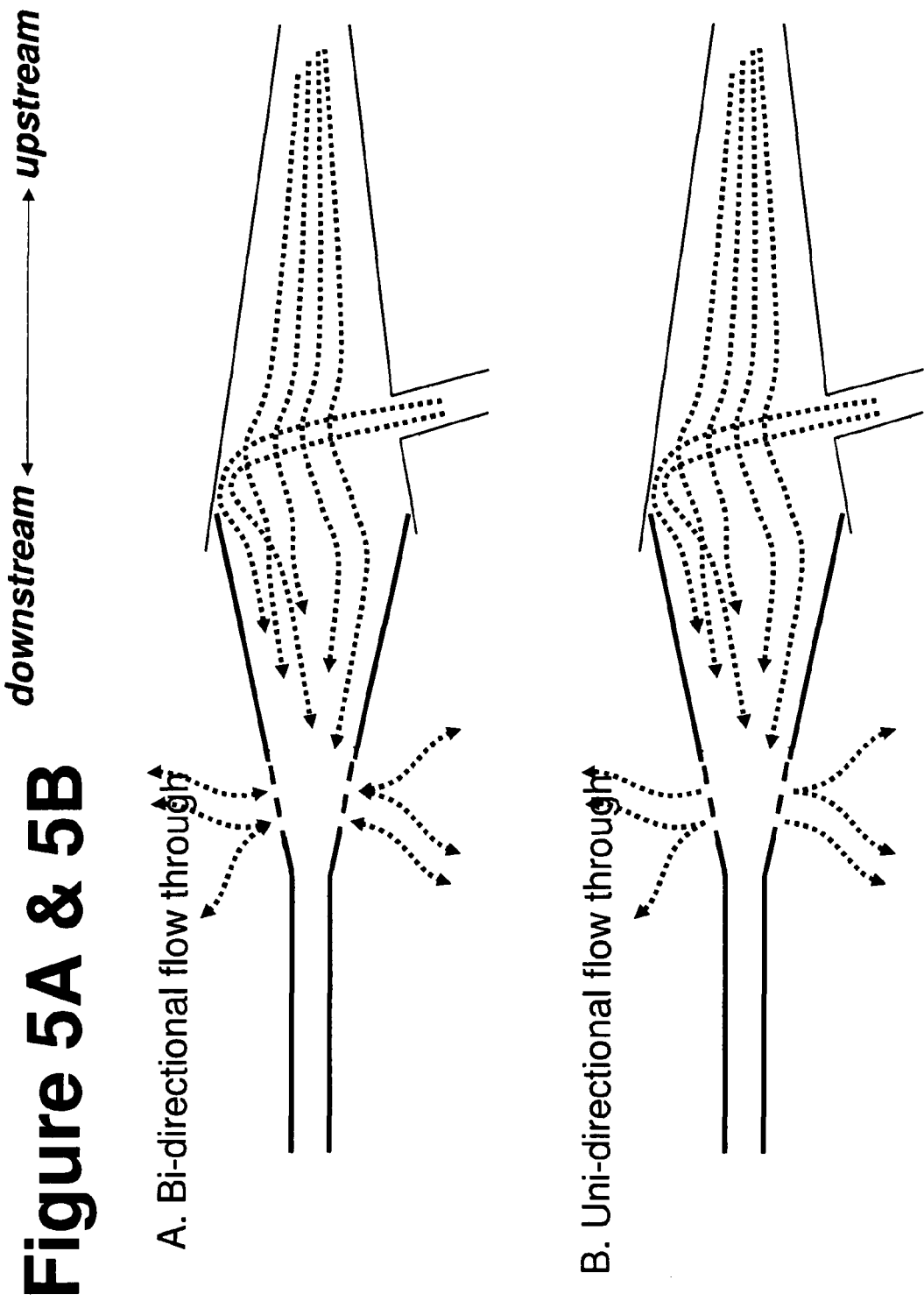

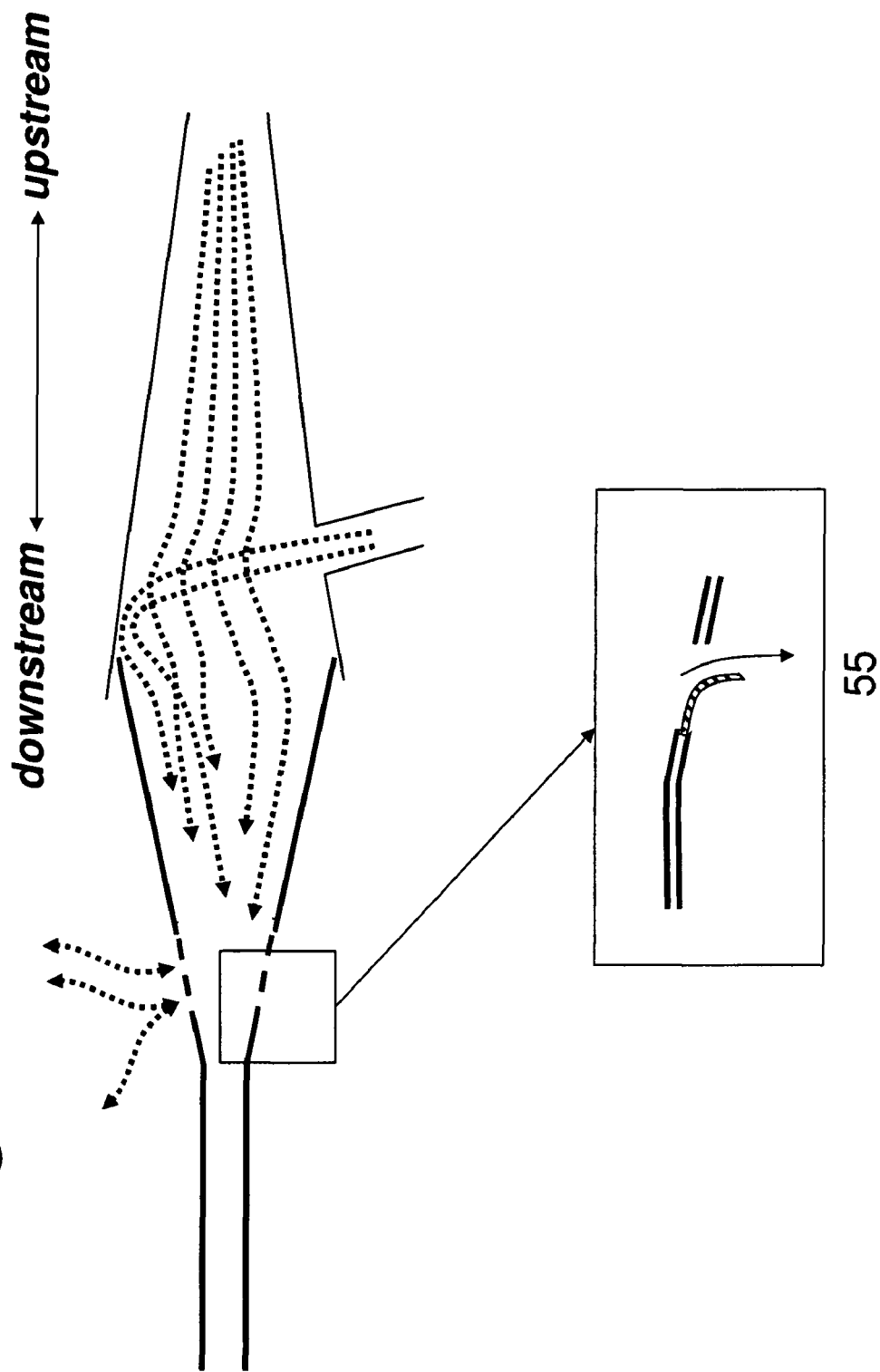

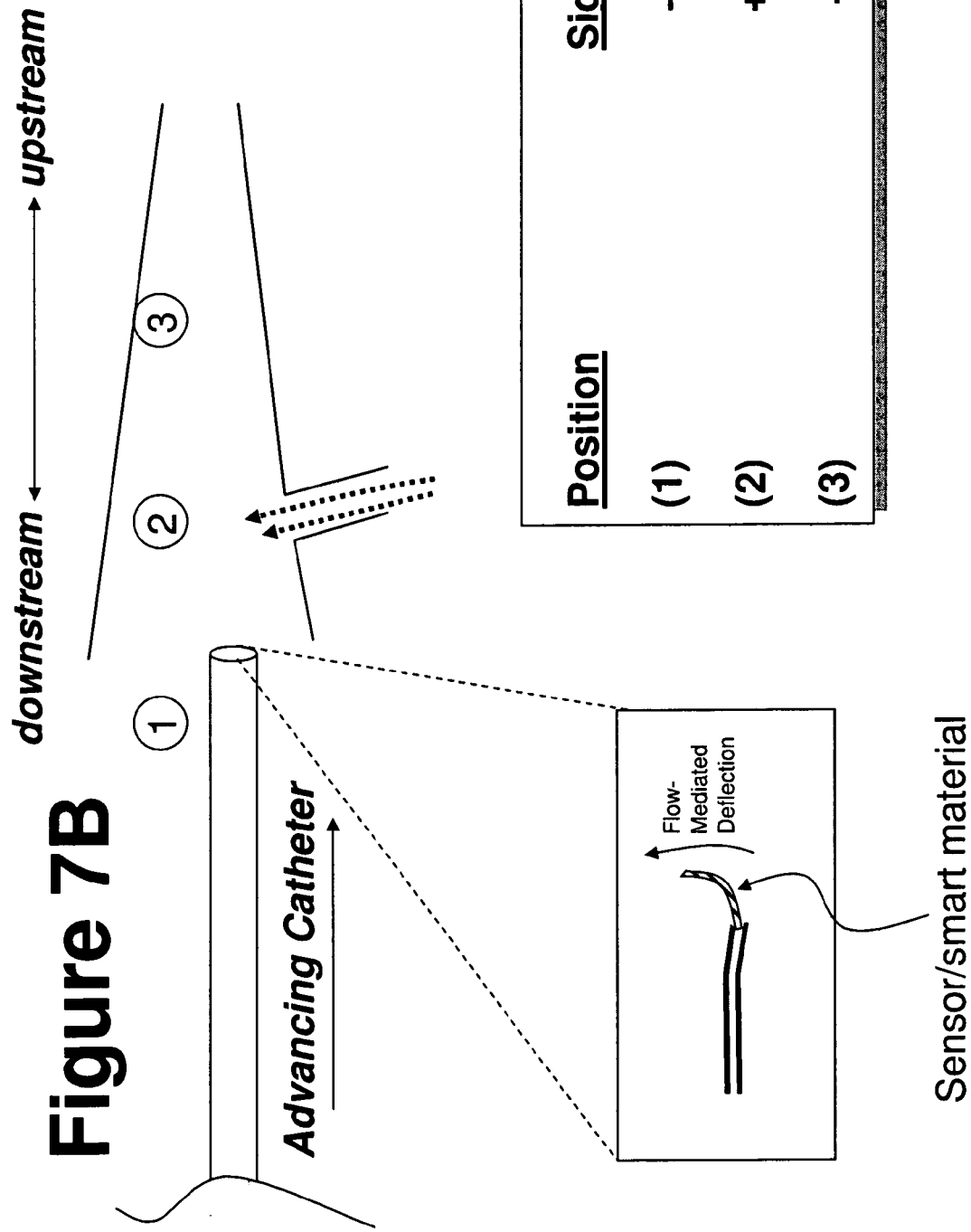

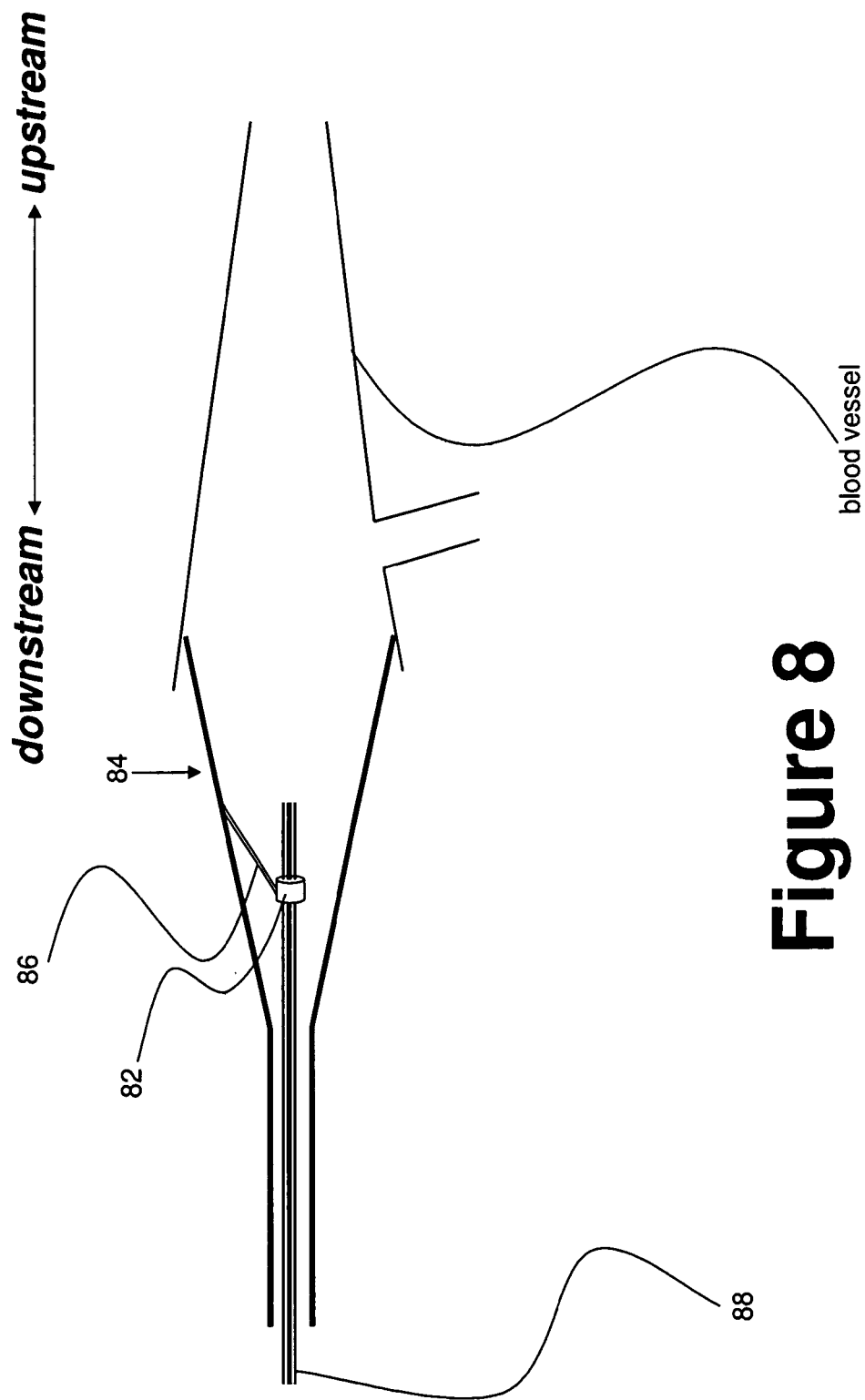

Detection In Glass Heart
*Methods:* Mapping Planes

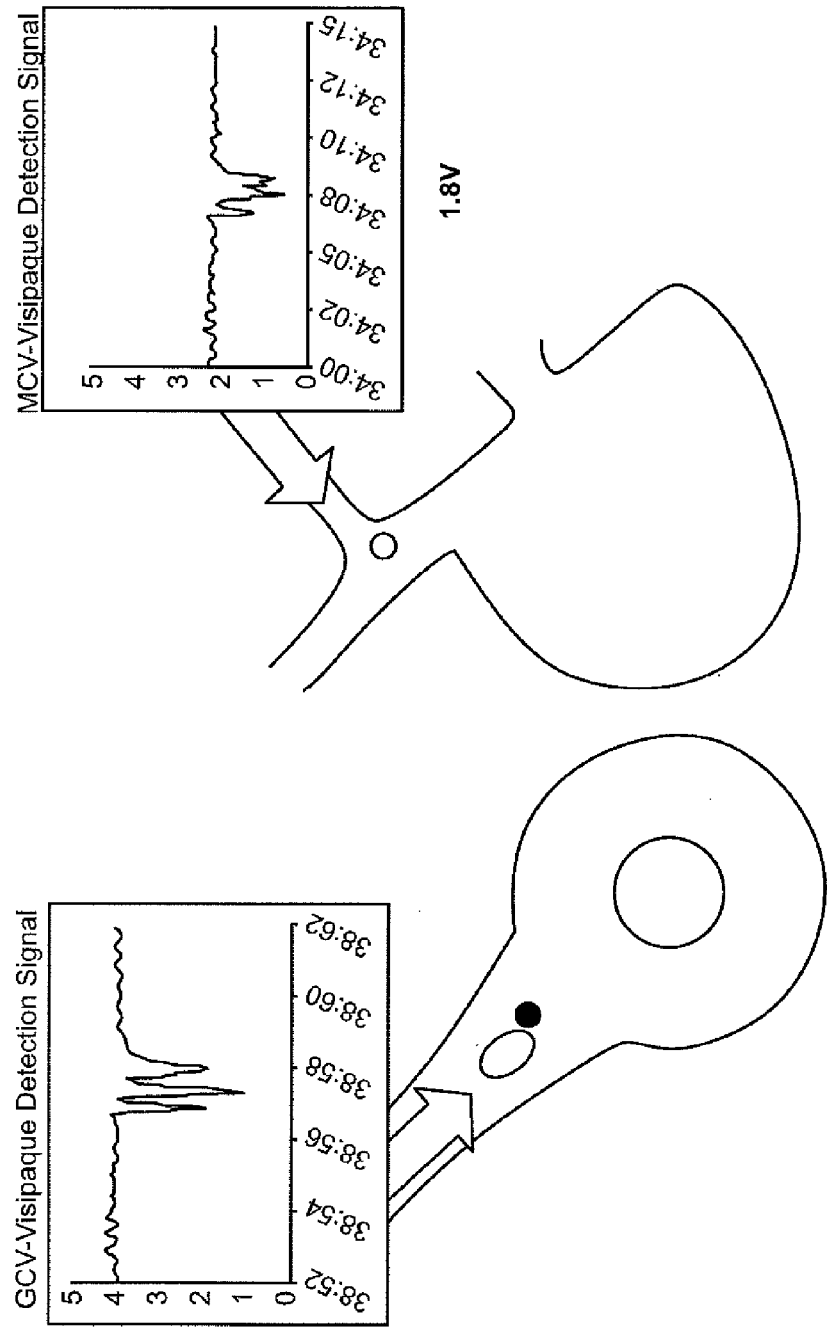

US 8,308,673 B2

METHODS AND DEVICES FOR REMOVAL OF A MEDICAL AGENT FROM A PHYSIOLOGICAL EFFERENT FLUID COLLECTION SITE

CROSS-REFERENCE TO RELATED APPLICATIONS

Pursuant to 35 U.S.C. §119(e), this application claims priority to the filing date of U.S. Provisional Patent Application Ser. No. 60/934,511 filed Jun. 13, 2007; the disclosure of which application is herein incorporated by reference.

INTRODUCTION

Administration of therapeutic or diagnostic agents to a subject is typically accomplished by either localized or systemic routes. With many types of agents, localized delivery methods are desirable. For example, medical compounds of interest may have desired diagnostic or therapeutic effects within the region into which they are introduced, but also exhibit toxic or other undesirable effects when they are allowed to circulate elsewhere. In certain cases, it is desirable to introduce a higher volume of a compound to the local region than can be tolerated by other body tissues if that volume were to ultimately cause the systemic concentration to exceed a safe threshold.

A common example of such a compound is radio-opaque dye. Iodinated forms of such a dye are used routinely during catheter-based interventional procedures such as coronary, renal, neurological and peripheral arteriography.

The iodine component has a high absorption of x-rays and therefore provides a contrast medium for the radiological identification of vessels when introduced within an upstream artery. However, the use of such dyes is known to have potential toxic effects depending on the specific formulation, including direct injury to renal tubule cells, endothelial injury, bronchospasm, inflammatory reactions, pro-coagulation, anti-coagulation, vasodilation and thyrotoxicosis.

Other materials that may be introduced locally for desired effects but whose direct or other effects would be undesired elsewhere include vasoactive agents, cytotoxic agents, genetic vectors, apoptotic agents, anoxic agents (including saline), photodynamic agents, emboli-promoting particles or coils, antibodies, cytokines, immunologically targeted agents and hormones.

An important anatomic concept with respect to the vasculature and other conduits supplying and draining an organ is the principle that a tissue or organ and regions of the organ have a limited number of primary supply conduits and a limited number of draining conduits. Material introduced into the upstream side of the target tissue will typically be dispersed among the diverging arterioles and capillaries, which then converge into a collection of common venules and vein (s) downstream, e.g., in a physiological efferent fluid collection site. For example, the myocardium of the heart is fed by the right coronary, left anterior descending and left circumflex arteries. Each of these arteries enters a capillary network that eventually converges into the small and middle cardiac vein, anterior interventricular vein and posterior vein of the left ventricle. These veins are all tributaries of the coronary sinus, which may be viewed as a cardiovascular efferent fluid collection site. Material introduced into any of the aforementioned coronary arteries that travels through the capillary network will enter the coronary sinus providing an opportunity to collect it before it returns to the systemic circulation. In another example, the brain is fed by the carotid and vertebral arteries which enter a highly anastomotic network. Blood flow through the brain substantially drains to the systemic circulation via a network of sinuses that converge onto the internal jugular veins. In yet another example, each kidney is substantially supplied by a renal artery and drained by a renal vein. In yet another example, a tumor or metastatic lymph node may have a set of primary afferent (supply) conduits and a set of primary efferent (drainage) conduits. In yet another example, the lungs are supplied by a pulmonary artery and its branches, and are drained by the pulmonary veins and their tributaries into the left atrium.

SUMMARY

Methods and devices for selectively removing an agent from a physiological site, e.g., a physiological efferent fluid collection site, are provided. Aspects of the invention include fluid removal (e.g., aspiration, devices having a fluid removal element and a flow modulator positioned at a distal end of the fluid removal element. The flow modulator is configured to converge intersecting fluid flow paths into the fluid removal element. Also provided are systems and kits for performing the subject methods. The subject invention finds use in a variety of different applications, including the selective removal of both therapeutic and diagnostic agents from a variety of different physiological sites.

BRIEF DESCRIPTION OF THE FIGURES

FIGS. 1B and 1C provide illustrations of physiological sites from which fluid may be removed according to certain embodiments of the invention.

FIGS. 2B to 2E provide different views of various flow modulator configurations according to certain embodiments of the invention.

FIG. 3 illustrates a device according to an embodiment of the invention.

FIGS. 4A to 4D illustrate fluid flow interactions with the device of FIG. 3 during various phases of use.

FIGS. 5A to 5C provide various views of fluid removal elements according to various embodiments of the invention.

FIGS. 7A and 7B provide various views of different sensor configurations that may be present in certain embodiments of the invention.

FIGS. 8 to 10 provide views of various positioning mechanisms that are found in certain embodiments of the invention.

FIGS. 11A to 11B provide different illustrations of an experimental configuration described in the Experimental section, below.

DETAILED DESCRIPTION

Figure 1A:
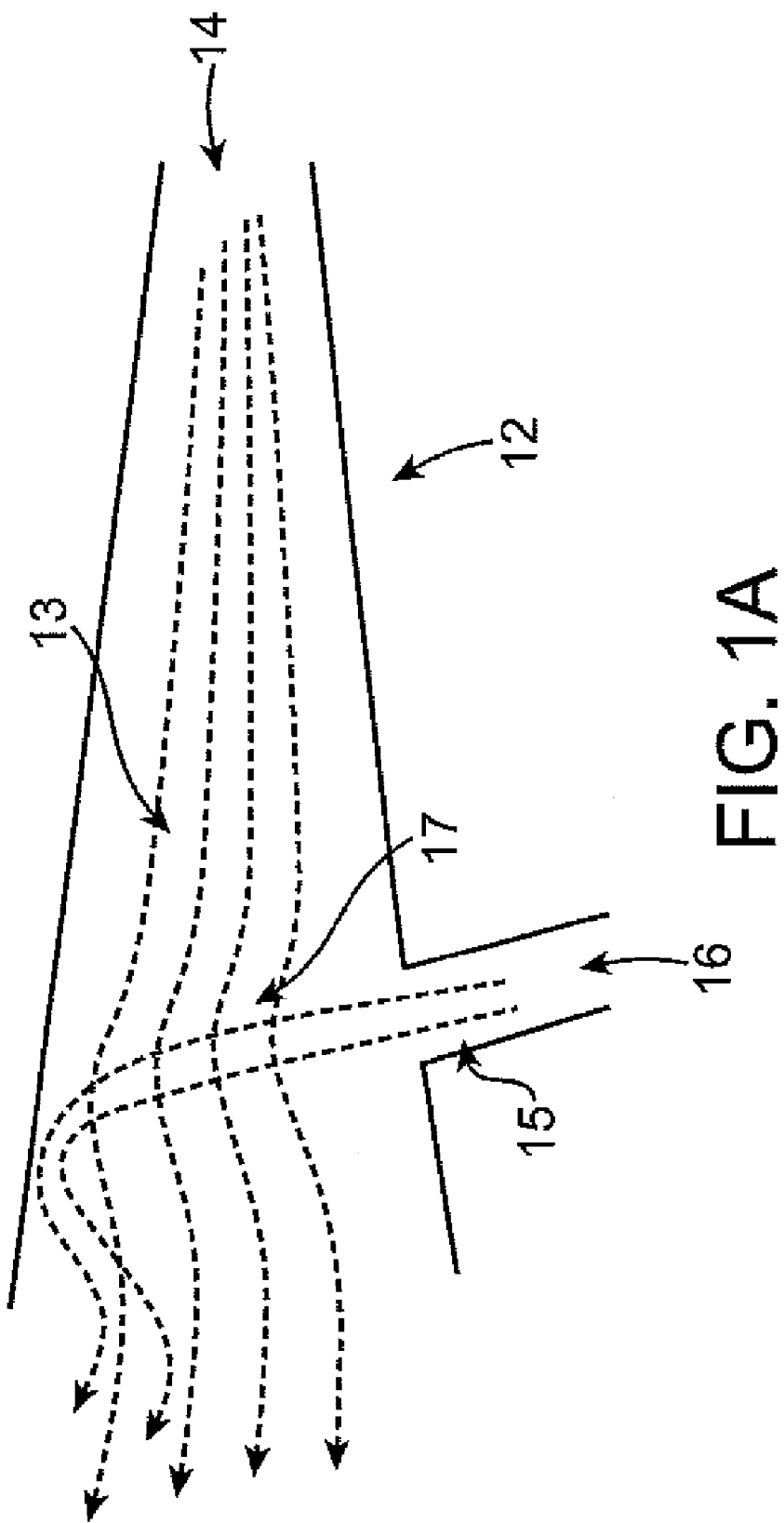
FIG. 1A provides a view of flow lamina in a coronary sinus, where the coronary sinus is an example of a physiological efferent fluid collection site.

Methods and devices for selectively removing an agent from a physiological site, e.g., a physiological efferent fluid collection site, are provided. Aspects of the invention include fluid removal (e.g., aspiration) devices having a fluid removal element and a flow modulator positioned at a distal end of the fluid removal element. The flow modulator is configured to converge intersecting fluid flow paths into the fluid removal element. Also provided are systems and kits for performing the subject methods. The subject invention finds use in a variety of different applications, including the selective removal of both therapeutic and diagnostic agents from a variety of different physiological sites.

Before the present invention is further described, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and Devices

As summarized above, aspects of the invention include methods for removing an agent from a physiological site, such as a physiological efferent fluid collection site, of a living subject. By physiological efferent fluid collection site of a living subject is meant a site in a living entity, where the site may be naturally occurring or artificially produced (such as by surgical technique), where fluid from at least two different sources or inputs combines or flows into a single location. An example of a physiological efferent fluid collection site is the coronary sinus, as illustrated in FIG. 1A, and described in greater detail below.

In certain embodiments, the physiologic site is not a physiologic efferent fluid collection site. For example, the site may be a site of a vessel in which agent is administered upstream of the site and then remove downstream of the agent introduction site, such the agent injection and collection sites are in the same anatomical vessel for a first vessel and a direct extension of the vessel. Examples of embodiments where the physiologic site of fluid collection is not an efferent fluid collection site are shown in FIGS. 1B and 1C. In FIG. 1B, vessel 1 bifurcates into side branch 2 and side branch 3. An agent may be injected upstream of the bifurcation, e.g., at point 4, and removed following bifurcation from each side branch by devices 5 and 6. FIG. 1 shows a variation in which vessel 1 is not bifurcated. Agent is introduced at location 4, detected at position 7 and removed at position 8.

The subject is generally an animal, where in certain embodiments the animal is a "mammal" or "mammalian." The terms mammal and mammalian are used broadly to describe organisms which are within the class mammalia, including the orders carnivore (e.g., dogs and cats), rodentia (e.g., mice, guinea pigs, and rats), lagomorpha (e.g. rabbits) and primates (e.g., humans, chimpanzees, and monkeys). In certain embodiments, the subjects (i.e., patients) are humans. In certain embodiments, the physiological efferent fluid collection site is a vascular efferent fluid collection site, where fluid from at least two different vessels joins into a single vessel. In certain embodiments, the vascular efferent fluid collection site is a cardiovascular fluid collection site, where fluid from at least two different veins joins into a single venous structure. In a specific embodiment of interest, the cardiovascular efferent fluid collection site is the coronary sinus. In yet other embodiments, as indicated above, the efferent fluid collection site may be an artificially, e.g., surgically, produced, fluid collection site, e.g., a non-naturally occurring fluid collection site produced by surgically joining two or more vessels together, etc.

In practicing embodiments of the subject methods, a fluid removal device, e.g., an aspiration device, is introduced into (i.e., positioned at), a target site. The target site is at least proximal to the physiological site, which may be an efferent fluid collection site and for ease of illustration is now further described as an efferent fluid collection site. By "at least proximal to" is meant that the target site is either upstream or downstream of the collection site, or the same as the collection site, so long as placement of the aspiration element at the target site provides for the desired removal of agent from the collection site upon actuation of the aspiration element, as described in greater detail below. In certain embodiments, the target fluid removal site is at a distance of 40 mm or less from the efferent fluid collection site, e.g., at a distance of 15 mm or less from the efferent fluid collection site.

Aspects of the fluid removal, e.g., aspiration device, include a fluid removal element, e.g., aspiration element, and a flow modulator positioned at a distal end of the aspiration element. For ease of description, the fluid removal element is primarily referred to herein as an aspiration element. The flow modulator is configured to converge intersecting fluid flow paths into the aspiration element. By intersecting flow paths is meant flow paths that are not parallel, where the non-parallel flow paths may or may not intersect each other at a right angle. In certain embodiment, the intersecting flow paths are the product of two or more different tributary vessels into the efferent fluid collection site. An example of intersecting flow fluid flow paths as produced by two different tributaries of the coronary sinus is provided in FIG. 1. As can be seen FIG. 1, coronary sinus 12 has two tributaries 14 and 16 that provide for two intersecting flow paths 13 and 15 respectively. The intersecting flow paths intersect in the coronary sinus as shown by 17. As can be seen in FIG. 1, the intersecting flow paths intersect each other and result in divergent flow paths as they leave the coronary sinus.

As the flow modulator is configured to converge intersecting flow paths, intersecting flow paths are brought together or focused onto a common region, in contrast to the divergent trajectory that is observed in the absence of the flow modulator shown in FIG. 1.

Figure 2A:
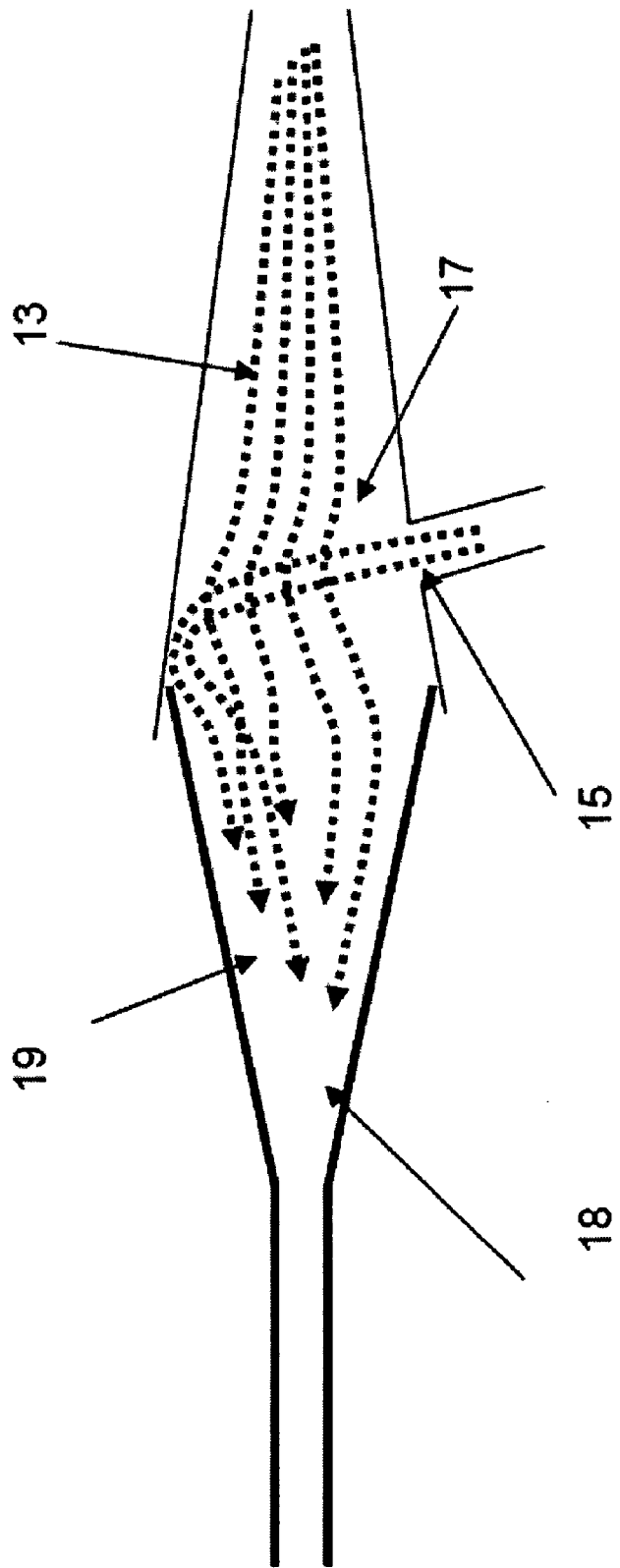
FIG. 2A provides a view of flow lamina in a coronary sinus that is redirected by a flow modulator according to an embodiment of the invention.

FIG. 2A provides a view of the effect of a flow modulator on the intersecting flow paths observed in a coronary sinus. In FIG. 2A, following the point of intersection of flow paths 13 and 15 at region 17, the intersecting flow paths are focused by modulator 18 to converge in region 19.

Figure 2B:
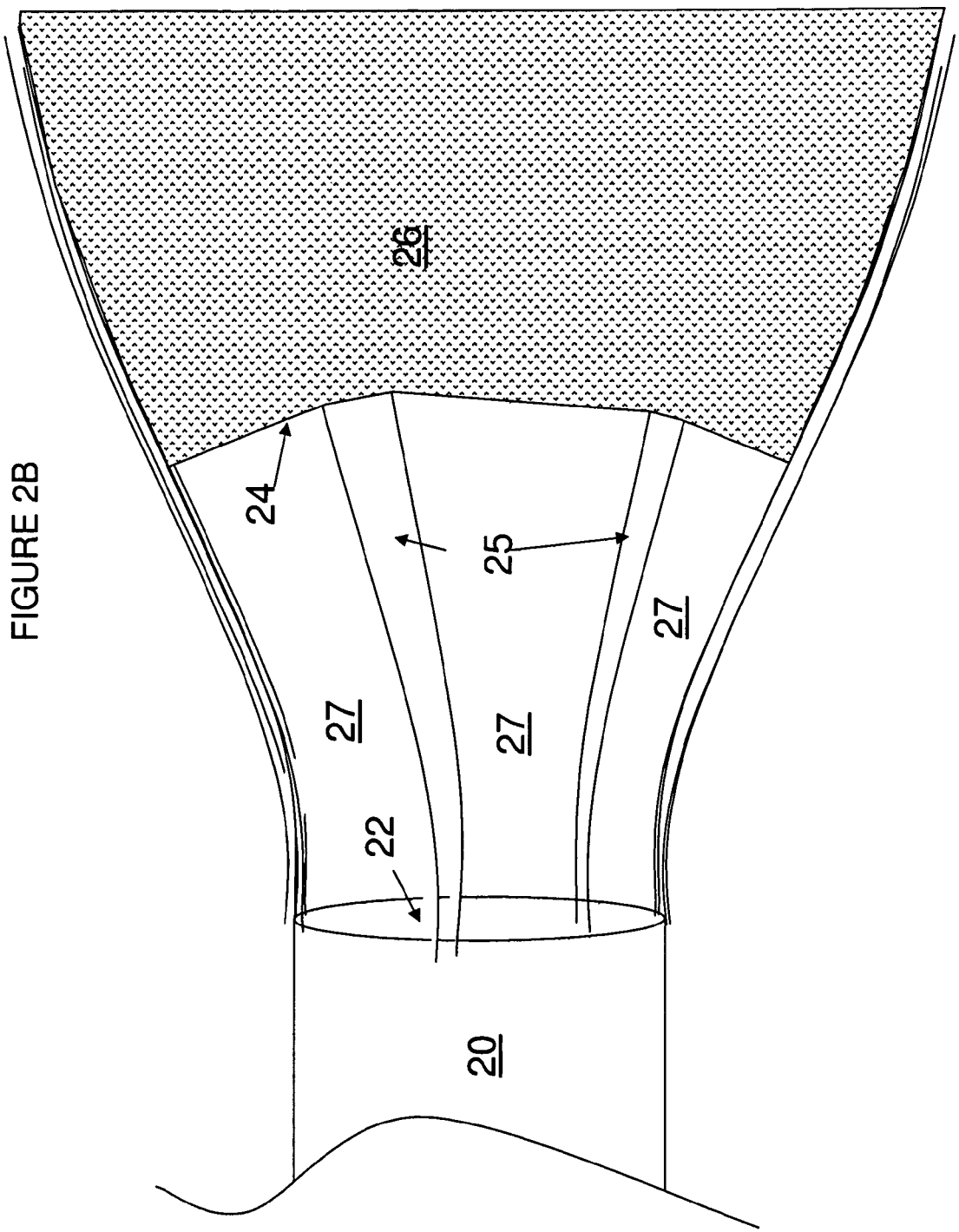
Figure 2C:
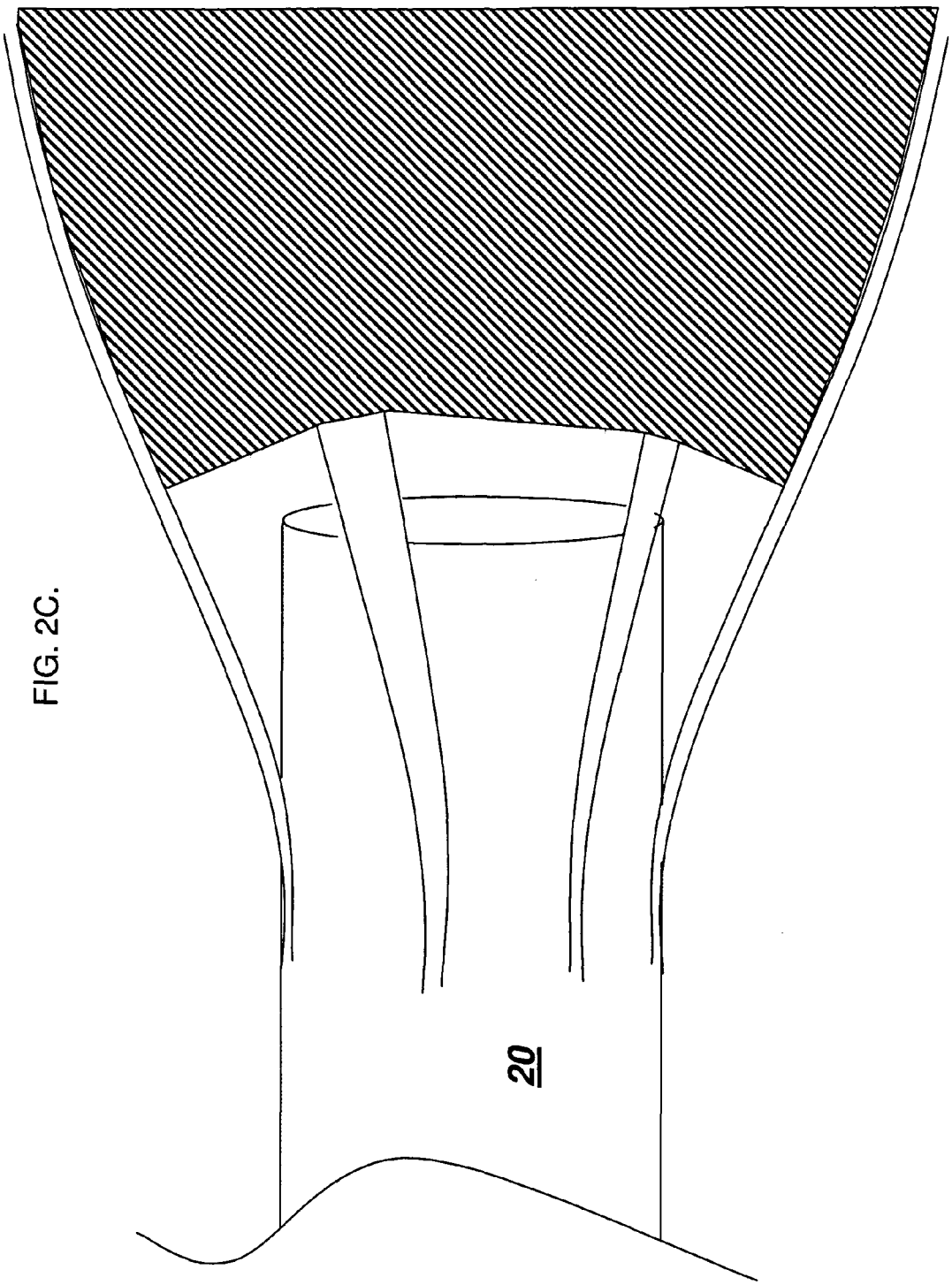

The flow modulators employed in embodiments of the invention may have any convenient configuration, so long as they operate to converge (i.e., focus) intersecting flow paths onto a defined region, such as the distal end of an aspiration element to which the flow modulator is operatively coupled. In certain embodiments, the distal end of the aspiration element is coupled to the end of the of the flow modulator such that it is not in direct fluid communication with the bounded space of the flow modulator. See e.g., FIG. 2B. In FIG. 2B, aspiration catheter has opening 22 which is positioned some distance from the end 24 of flow modulator 26. Attachment elements 25 hold flow modulator 26 in position relative to aspiration catheter 20 and openings 27 provide for fluid flow out of flow modulator 26 when negative pressure is not present in aspiration catheter 20. In the embodiment shown in FIG. 2B, the distal end 22 of the aspiration catheter is coupled to the proximal end 24 of the flow modulator in a manner such that the aspiration catheter is not in direct fluid communication with the lumen of the flow modulator. In certain embodiments, the distal end of the aspiration element is not coupled to the end of the of the flow modulator 26, but instead extends partway into the area defined by the flow modulator, i.e., the lumen, e.g., as shown in FIG. 2C. These different configurations can provide for different flow configurations as shown in FIGS. 2D & 2E, where a particular flow configuration may be desirable for a given application.

Following positioning of the aspiration element and flow modulator at the target site, the aspiration device is activated when the agent to be removed is at least predicted to be present in the target site. Activation occurs in a manner effective to remove fluid comprising the target agent from the subject. Embodiments are characterized in that the agent is selectively removed from the efferent fluid collection site. The flow modulator of the aspiration device may be positioned at any convenient location, so long as it serves to converge intersecting flow paths as desired. In certain embodiments, the flow modulator is positioned at an intersection of two or more tributaries of the physiological efferent fluid collection site, e.g., where main (or axial) and side (or radial) flow paths intersect.

As reviewed above, aspects of the invention include the selective removal of agent from the efferent fluid collection site. By "selectively removed" is meant that the subject methods remove fluid from the target site in a manner that selectively or preferentially removes fluid that is at least predicted to include the agent, where the removed fluid is not returned to the body, at least not without processing to remove the target agent present therein. (In certain embodiments the removed fluid is simply disposed of, such that the methods include a step of disposing of the removed fluid, while in other embodiments the fluid is processed (e.g., filtered) and then returned to the subject, as reviewed in greater detail below). Depending on the particular protocol and device employed, as described in greater detail below, the fluid may be continuously collected at the fluid collection site but not removed from the body unless it is at least predicted to include agent, e.g., as occurs in those embodiments where fluid is collected at the fluid collection site but immediately shunted back to the subject if it is not at least predicted to include agent. By "at least predicted" is meant that the bulk or majority of the fluid removed from the site is fluid that is either anticipated to include the agent, e.g., fluid in which the presence of the agent is inferred, or fluid that is known to include the agent, e.g., fluid in which the presence of the agent is detected. Depending upon the particular embodiment of the invention being practiced, in selectively removing fluid from the target fluid collection site and subject, fluid may be removed from the site and subject for a period of time which commences prior to when agent is at least predicted to be in the site, and extend for a period of time after agent is at least predicted to be in the site. In such embodiments, the period of time during which fluid is collected before and/or after agent is at least predicted to be in the site is a fraction or portion of the total period of time during which fluid is removed, typically being less than 50%, such as less than 25% including less than 10-15% of the total time period during which fluid is removed.

In certain embodiments, the subject methods do not remove all fluid from a target and efferent fluid collection site, but just fluid that is at least predicted to include the target agent of interest. In other words, in practicing the subject methods, not all fluid from an efferent fluid collection site present over a given period of time is removed, only fluid that is at least predicted to include the target agent of interest that is to be removed. Put another way, over a given period of time where fluid that does and does not include the target agent flows through the efferent fluid collection site and/or a target fluid collection site, only fluid that is at least predicted, e.g., is anticipated or known to include the agent, is removed from the site and subject, while fluid that does not likely include the target agent is preferentially not removed from the site and subject.

Another aspect of certain embodiments of the subject methods is that, in certain embodiments, not all of the agent that is administered prior to practice of the subject methods is removed from the subject. In other words, only a portion of the administered agent is removed from the host or patient by the subject methods. By portion is meant at least about 20%, usually at least about 50% and more usually at least about 70% of the administered agent is removed by the subject methods, where in certain embodiments, the portion removed is at least about 75%, at least about 80%, at least about 90% or more. However, as not all of the agent is collected during practice of embodiments of the subject methods, in certain embodiments at least 1% of the originally administered agent remains in the subject or patient, such as at least about 5% or at least about 10%.

Agent is selectively removed from the target site, which may or may not be the efferent fluid collection site, according to the subject methods by removing, e.g., aspirating, fluid from the target site and subject, substantially only when the target agent is at least predicted to be present in the target site, as described above. As such, when agent is at least predicted to be present in the target site, fluid is removed from the site and subject. Conversely, in certain embodiments when agent is not predicted to be present in the site, fluid is not removed at least from the subject, and in certain embodiments not from the site. Accordingly, in certain embodiments, upon detection or anticipation of agent in the fluid collection site fluid is removed or aspirated from the site and subject, while when the target agent is not detected or anticipated to be present in the site, fluid is not removed from the site, with the exception of a short period of time before and/or after the time when agent is at least predicted to be in the target site, as described above.

In certain embodiments, fluid is selectively removed by actuating a fluid removal element, e.g., aspiration device, such as the devices described below, a defined period of time following administration of the agent to the subject, e.g., an absolute preset period of time, a period of time as defined by a physiological metric, e.g., heart beat, etc.

In certain embodiments, the methods include a detection step, where a procedure relevant parameter is detected using an appropriate sensor (i.e., detector) element. A variety of different procedure relevant parameters may be detected, as desired. Such parameters include, but are not limited to: the agent itself (which may be detected both directly and/or indirectly), flow dynamic, e.g., hemodynamic parameters, anatomical parameters, etc. A variety of sensors may be employed, including but not limited to: impedance sensors, ultrasound sensors, Doppler sensors, optical sensors, etc.

In certain embodiments, the methods include a step of detecting one or more fluid flow parameters, such as hemodynamic parameters. For example, fluid flow may be assessed at various locations of an efferent fluid collection site during a given protocol. With respect to the coronary sinus, fluid flow may, for example, be assessed at the flow outlet of the flow modulator to the aspiration element (e.g., to provide activation efficiency of aspiration) and/or at the ostium (OS) of the coronary sinus (e.g., for assessing reflux from the right atrium). A variety of different types of flow dynamic sensors may be employed, as desired, where such sensors include deflection sensors, thermal sensors, sensors of oxygen contents e.g., that provide an assessment of flow direction or orifice of a tributary during device insertion, etc.

In certain embodiments, the methods include a step of detecting anatomical structures or features, e.g., to assist in proper placement of the device at the target site. For example, detectors for assessment of branching points of tributaries of interest (e.g., middle cardiac vein, posterior vein of left ventricle, lateral vein of left ventricle, and other vascular tributaries) may be employed (e.g., to aid in axial positioning of the device at the target site). Examples of such detectors include flex detectors (e.g., as described in United States Published Application No. US-2006-0173365-A1), in which bending of a material causes signal generation that can be used to determine when the structure passes a certain anatomical feature of interest. Another type of detector that may be employed for this purpose is an EKG detector, which uses the distinct EKG signatures associated with anatomical transition points, such as the entry to the coronary sinus, to determine location of the catheter in the vessel and aid in placement at the desired location.

Additional detectors may be employed, where desired, to provide data which can be employed to modulate operating parameters of the device during aspiration, e.g., aspiration rates, etc. For example, EKG activity may be detected to obtain reference time-points for adapting aspiration rates to the instantaneous flow inside the target site, as the flow in the target site may fluctuate as various time points during the EKG cycle. In addition, pressure detectors, e.g., for assessment of vacuum efficiency or for detecting CS-pressure signature during device insertion, may be employed, e.g., to provide data which may be used to modulate evacuation rates. Likewise, flow detectors for assessment of baseline flow rate may also be employed for similar purposes.

In certain embodiments, the methods include a step of detecting the presence of target agent in the site and then removing fluid, and agent present therein, from the site in response to detection of the presence of target agent in the site. As reviewed in greater detail below, the presence of the agent may be detected directly or indirectly. Typically, when agent is no longer detected in the efferent fluid collection site, the methods stop removing fluid from the site. Thus, fluid is only removed from the efferent fluid collection site and subject over a time period that substantially overlaps the period in which the target agent is present in the efferent fluid collection site.

In practicing these embodiments of the subject methods, the agent may be detected in the fluid collection site using a number of different protocols. In certain embodiments, agent is visually detected by a skilled operator, who then removes fluid in response to visualizing agent, e.g., according to the protocols described below, present in the fluid collection site. In yet other embodiments, agent detection devices that are operatively connected to a fluid removal device are employed, where a signal from the detector that agent is present in the fluid collection site automatically actuates a fluid removal device, e.g., aspiration unit. Representative embodiments of devices that may be employed in such embodiments are described in greater detail below.

In certain embodiments, the system includes a detector (i.e., sensor) component, e.g., for detecting the agent of interest (or a proxy therefore). The agent of interest may be detected using a number of different approaches. In certain embodiments, properties of the agent itself are detected. For example, specific binding of the agent may be employed, e.g., using a binding event sensor; optical/photometric approaches for detecting the agent, e.g., reflectance, transmission, evanescence, etc., may be employed; physical, e.g., viscosity, changes caused by the agent may be employed; electrical, e.g., conductivity, changes caused by the agent may be employed; radioactive, e.g., radiosorbance, approaches may be employed; fluorescence changes caused by the agent may be employed; acoustic, e.g., ultrasonic: echogenicity, scattering, etc. changes caused by the agent may be employed, etc.

In certain embodiments changes in the fluid caused by the presence of the agent are employed to detect the presence of the agent. Changes of interest in a given fluid include, but are not limited to: changes in number of blood cells per volume; changes in optical properties; changes in chemical properties; changes in physical properties (density, hematocrit, viscosity); changes in hemodynamic properties (velocity); changes in overall imaging properties of blood (ultrasonic, radioactive, radiosorbent, fluorescent, etc.

To aid in the detection of the agent, in certain embodiments the agent will be one that is labeled with a detectable label, e.g., agent that is has been labeled with a detectable label prior to its introduction into the patient. The agent may be directly labeled with the detectable label, or associated with a detectable label such that the agent is indirectly detectable in that detection of the label also indicates the presence of agent which is presumed or inferred to be within the vicinity of the label. The nature of the label may vary, and may be a radio label, fluorescent label, chromogenic label (e.g., that has a pigment detectable in the optically visible spectrum), etc.

In certain embodiments, the pressure of the target site and/or efferent fluid collection site (which may or may not be the same locations, as described above) and or the tributaries thereof, including a subset of the tributaries thereof, may be modulated, e.g., reduced, in order to achieve the desired collection of agent from the host. The manner in which the pressure may be modulated may vary depending on the particular device employed and manner in which it is implemented, where representative devices and protocols capable of pressure modulation of the target/efferent fluid collection site are described in greater detail below. By modulating the pressure in this manner, one can reduce the pressure within the collection site sufficiently to improve the efficacy of removing the desired agent without causing collapse of the tributaries of the efferent fluid collection site, resulting in a better favorable outcome of the method.

In certain embodiments, devices that include a shunting element, be it a passive or active shunting element, are employed in a manner that modulates the pressure of the target site and/or efferent fluid collection site, as desired. Alternatively and/or in addition thereto, one can use of a pressure sensor within the fluid collection site. The output from such a sensor may be used to optimize the maintenance of the pressure in the collection site so that it is reduced sufficiently in order to increase the likelihood of higher flow to that region from those tributaries that have alternative paths, without causing the collapse of such tributaries.

In certain embodiments, an extension of an aspiration lumen of the device employed is extended selectively into one or more tributaries in order to prevent their collapse during aspiration and to extend the volume from which fluid is aspirated. Alternatively, rather than using a lumen to structurally support the tributaries, a temporary or permanent stent could be introduced to those tributaries prior to aspiration.

In certain embodiments, a specific pattern of aspiration rates that compensates for the delay time between the detection of the desired agent and the activation of the aspiration mechanism is employed. For example, in certain embodiments, there will be a small but finite delay in time between when the agent enters the fluid collection site and when the aspiration mechanism begins to aspirate fluid from the site. During this time delay, some of the fluid containing the agent may have already passed the region from which aspiration normally occurs at the distal portion of the aspiration lumen, thus potentially reducing the efficacy of retrieving the agent. However, by having a higher rate of aspiration for the early portion of the period in which aspiration occurs, as compared to a rate that more closely resembles the normal physiologic rate of flow within the collection site, e.g., where the higher aspiration rate is 2-fold greater, such as 5-fold or 10-fold greater or more, one can cause that fluid which has already passed the region from aspiration to change direction and return to the aspiration ports. Once this initial period of a higher rate of aspiration has expired, the aspiration rate could then occur at a lower rate which more closely approximates the normal physiologic rate of flow within the collection site, as desired. Varying aspiration rates maybe required at sites where inflow from tributaries follows a cyclical patterns. A typical example is the inflow from the middle cardiac vein into the coronary sinus, where peaks are registered during systole, and lows during diastole. For this purpose, EKG triggering of aspiration may be employed.

In some embodiments, more than one kind of detector is employed to determine the aspiration parameters and time period. For example, in order to ensure that the leading edge of the agent is successfully aspirated, the activation of the aspiration mechanism may be activated by a counter that counts a conservative, pre-selected number of QRS complexes on an EKG after the beginning of injection of the agent, while the trigger to deactivate the aspiration mechanism may be derived from an optical sensor that can recognize when there is no longer any more agent within the fluid being aspirated. Alternatively, inputs from more than one detector can be used in direct combination with each other to determine the aspiration parameters. For example, due to cardiac motion in the region of a fiber optic based sensor, and/or variations in the rate of flow of the fluid in the region of the sensor, the signal produced may vary in a pattern that is reflective of the cardiac cycle, regardless of whether or not the agent to be detected is present, thus producing a noisy signal. In such a case, the fidelity of the sensor may be augmented by using a filtering algorithm that uses the input from an EKG signal to filter the signal produced by the optical detector. By compensating for changes to the output of the optical detector that are due to the cardiac cycle, it may be easier to more accurately characterize the concentration of the agent to be removed in the region of the detector. Any of the detectors mentioned below may be suitably used in combination with each other to further optimize the detection process and/or the efficacy of the aspiration controller. In certain embodiments, a feedback from the agent injection system can be incorporated into the signal processing algorithm, which ultimately leads to commencement of aspiration.

Practice of the subject methods results in selective removal of an agent from a fluid collection site and subject (also referred to herein as patient or host), where the amount of agent removed is, in certain embodiments, a substantial portion of (but not all of in certain embodiments) the agent that is present in the subject, as described above.

In certain embodiments, the fluid that is removed from the subject or patient may be treated extracorporally, e.g., to remove or neutralize the agent, and then reintroduced into the subject, e.g., where it is desired to minimize the ultimate or final volume of fluid, e.g., blood, that is removed from the subject in a given procedure. For example, where the fluid removed from the subject is blood, the removed blood may be processed with a blood filtering device to remove the agent from the blood, and the processed blood, or at least a component thereof (such as red blood cells) be returned to the patient. Examples of fluid, e.g., blood, processing devices include, but are not limited to: the Cell Savers device (available from Haemonetics); autoLog (available from Medtronic); and the like.

As such, the subject methods may include a step of transferring the harvested fluid into a recirculating system to be reintroduced into the body (as described in U.S. Pat. No. 5,925,016, the disclosure of which is herein incorporated by reference). The recirculating system may incorporate mechanisms to separate the substantially undesirable components from the substantially desirable components. Such a system may incorporate a filter, a centrifugal separator, flow cytometry, apheresis or other similar apparatuses. The aspiration mechanism may incorporate fluid characterization elements by which aspirated fluid may be characterized, either quantitatively or qualitatively.

Accordingly, in certain embodiments the subject may be one in which it is desired to keep blood loss at a minimum, e.g., the patient may suffer from coronary artery disease, chronic anemia, etc. Extracorporeal processing and subsequent reinfusion of the treated fluid allows for the reintroduction of the desirable components as an autologous transfusion. Centrifugal mechanisms, filter-based systems, dialysis membranes and cell-washing mechanisms are examples of some functional components that can be employed for this purpose.

The methods may be carried out using any convenient system/device, where in certain embodiments, catheter based systems/devices are of interest. Embodiments of aspiration devices and systems thereof for use in practicing the subject invention are reviewed in greater detail in the following section.

As summarized above, the aspiration devices employed in methods of the invention include an aspiration element having a proximal and distal end, and a flow modulator present at the distal end of the aspiration element.

With respect to the aspiration element, this element may include one or more aspiration lumens, where the aspiration lumen(s) is constructed or configured in such a manner to be introduced into the target collection site, e.g., efferent fluid collection site or a site proximal thereto, e.g., via a body conduit such as the venous vasculature, so that the distal end of the lumen can be positioned in the target site for collection of the introduced medium. In certain embodiments where the target efferent fluid collection site is a cardiovascular efferent fluid collection site, e.g., as in the case of retrieving compound-laden fluid from the coronary sinus, there may be a catheter with a length appropriate for introduction through either a brachial, subclavian, jugular or femoral access site to be advanced to the coronary sinus, likely over a guidewire or similar element, for percutaneous delivery. In these embodiments, the aspiration lumen is a catheter device, having dimensions sufficient to be introduced into the efferent fluid collection site via a vascular, e.g., venous route, where such dimensions are known and readily determined by those of skill in the art.

In certain embodiments, the aspiration lumen has more than one diameter along its length. For example, in order to more easily to enter or approach a collection site, the distal portion of the aspiration catheter is of a first diameter such that the distal portion fits within the geometric constraints of the anatomy of the collection site. In order to reduce the resistance to flow along the entire length of the aspiration lumen, the aspiration lumen has a second, larger diameter for one or more proximal segments of the aspiration lumen. In some cases where a high degree of flow may be required in order to successfully aspirate all the fluid that enters the collection site, such a configuration helps to reduce the total resistance of the lumen, which is proportional to the fourth power of the radius and is thus very sensitive to lumen diameter.

In certain embodiments, the inner surface of the lumen may be shaped, e.g., to promote aspiration along the length of the element. For example, the inner surface may have a spiral configuration, e.g., a spiral ridge, on the inner surface of the lumen.

The aspiration lumen is, in certain embodiments, specifically constructed to be non-occluding. As such, the aspiration lumen of these embodiments does not include an occlusive element, e.g., a balloon or other element designed to occlude a vessel or conduit. As such, the subject devices of these particular embodiments are occlusive element-free devices.

Positioned at the distal end of the aspiration element is a flow modulator. An example of a flow modulator is depicted in FIG. 2A. In FIG. 2A, the flow modulator is configured so that, when deployed, it produces a flared end at the proximal end of the aspiration element. Not shown in the structure of FIG. 2A are flow shunt elements which make up a flow outlet and provide for an exit for fluid flow when aspiration is not occurring.

Another example of a flow modulator of interest is one that includes an expandable frame of two or more longitudinal elements. FIG. 3 provides a view of an embodiment of such a flow modulator. In FIG. 3, an aspiration device that includes an aspiration element (in the form of an aspiration catheter) 32 and a flow modulator having an expandable frame 36 at its distal end is positioned in the coronary sinus. The region where the flow modulator is joined to the distal end of the aspiration element is referred to herein as the "flow outlet" 40. The expandable frame includes two or more longitudinal elements 33, where the embodiment shown in FIG. 3 has 6 longitudinal elements. The longitudinal elements may be any convenient structure, including a resilient monofilament, which may fabricated from a material such as Nitinol, stainless steel, cobalt-chromium alloys, and the like.

While the overall frame shape may have any convenient configuration, in certain embodiments the frame shape is cylindrical or substantially cylindrical. Of interest are frame shapes that have tapered (i.e., infundibular) shape at their proximal end, which shape can provide for certain advantages, e.g., reversal of unfavorable anatomical tapering, such as venous tapering. Also, when a centering mechanism for the detector is employed with such configurations, this configuration can ensure that the centering mechanism positions the detector at a desired location in the flow modulator so that optimal detection can be achieved.

Positioned between the longitudinal elements of the flow modulator of FIG. 3 is an impermeable membrane 34. The impermeable membrane is positioned between two or more longitudinal elements, including all of the longitudinal elements as shown in FIG. 3. The impermeable membrane 34 may be fabricated from any convenient material, including but not limited to polyurethane, polyester, polyethylene and other polymer-based materials with a certain degree of elasticity, and the like. While the membrane may define a variety of configurations, in certain embodiments such as the one shown in FIG. 3, the impermeable membrane is configured to produce an asymmetric fluid barrier upon expansion of the expandable frame. By asymmetric is meant that the membrane does not define a bounded region of uniform axial length. The membrane 34 is bounded at the distal end by flow inlet 38 and at the proximal end by flow outlet 40.

In practicing the invention, following positioning of the distal end of the aspiration device (that includes the aspiration element a flow modulator) at the target site, the flow modulator is deployed, e.g., by expanding the frame at the target site (which includes the site of intersection of the fluid flow paths). Deployment may be by passive or active mechanism, as desired. For example, the expandable frame may be fabricated from a shape memory material, e.g., Nitinol, shape-memory and/or super-elastic materials, which is compressed during delivery and then the compressive force on the frame is removed to deploy the frame.

The embodiment shown in FIG. 3 includes an aspiration element and flow modulator which are configured so that fluid flows past the aspiration element when the aspiration element is not activated. In the embodiment shown in FIG. 3, the flow modulator includes a flow outlet 40 positioned downstream of membrane at the coupling region of the expandable from and the distal end of the aspiration element. When the aspiration device is not activated, e.g., when agent is not at least predicted to be present at the target site, fluid flows out of the flow outlet.

The configuration of the membrane in the embodiment of FIG. 3 provides for the desired convergence of fluid flow lamina that originate in both axial and sidewise (i.e., radial) directions, as illustrated in FIG. 4A. As shown in FIG. 4A, the axial flow lamina from the main vessel tributary and the sidewise or radial flow lamina from the side branch tributary intersect within the region bounded by the impermeable membrane and are then converged or focused onto the distal end of the aspiration catheter 32. In this way, the flow modulator converges the intersecting flow paths or lamina of the main and side vessels entering the efferent fluid collection site, e.g., coronary sinus, onto the distal end of the aspiration catheter.

Figure 4D:
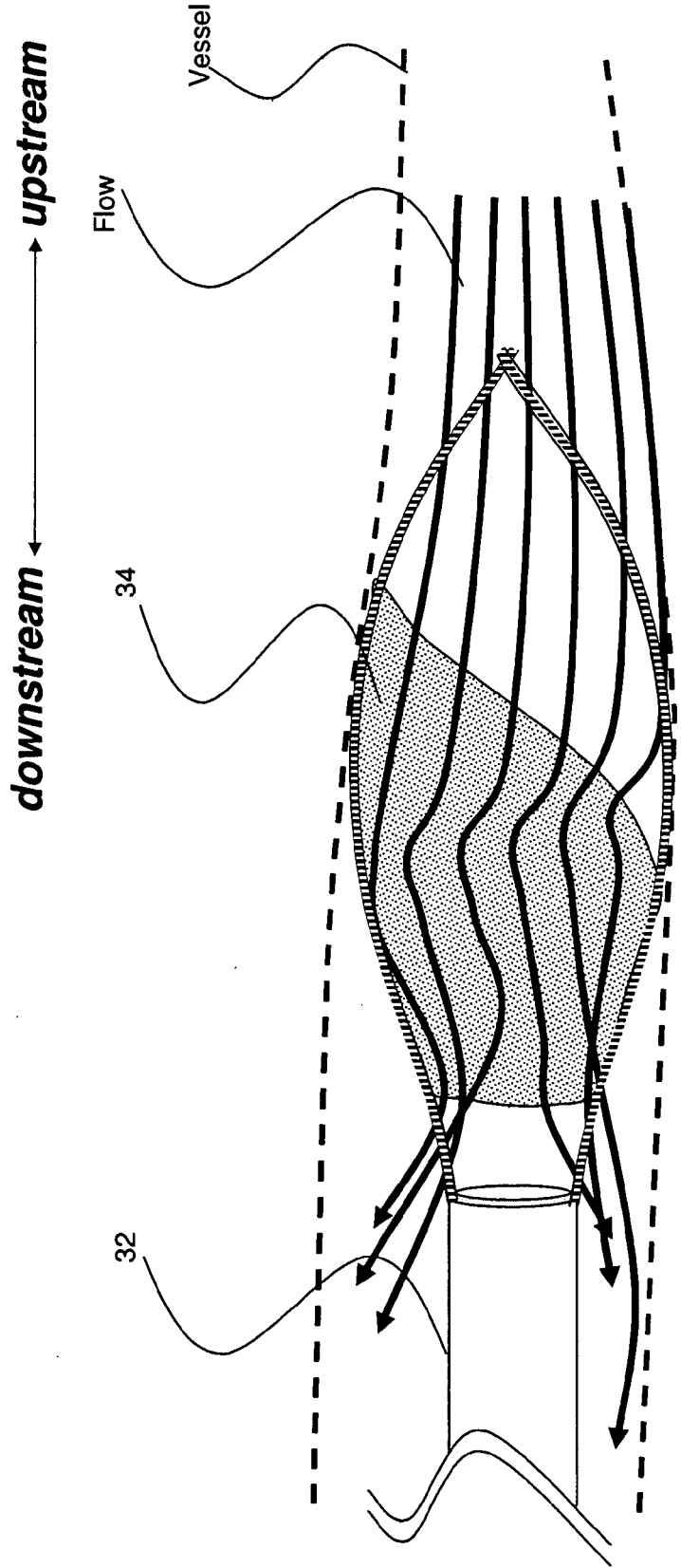

FIGS. 4B to 4D illustrate the function of a device according to an embodiment of the invention. As illustrated in these figures, the flow inside a blood vessel is typically phasic, with alternating phases of high and low flow. Assuming constant aspiration rates through the catheter, during periods of high flow rate as illustrated in FIG. 4B, the flow (a) enters the flow modulator tip of catheter, and is predominantly captured by aspiration (d). If the flow rates are higher than aspiration rates, the flow would exit (b) the flow modulator without being captured during this phase. In certain instances, the action of aspiration causes downstream flow to reverse following aspiration/pressure gradient. During period of low flow as illustrated in FIG. 4C, the slow/still flow (a, b) is mobilized and captured (d) as a result of the aspiration gradient. Assuming that aspiration rates are higher than flow rates during this phase, a portion of the down-stream flow can be reversed (c) and captured by aspiration, thus compensating for flow that has escaped aspiration during high-flow phase (FIG. 4B, item b). During periods of non-aspiration as illustrated in FIG. 4D, the flow passes through the flow modulator, and exits it without being captured by the aspiration catheter.

In certain embodiments, the flow outlet between the flow modulator and aspiration element may include features that provide for control over fluid flowing through the flow outlet. In certain embodiments, the flow outlet is configured to allow bidirectional fluid flow, as shown in FIG. 5A. In certain embodiments, the flow outlet is configured to allow for unidirectional fluid flow, as shown in FIG. 5B. Where desired, fluid flow through the flow outlet, either unidirectional or bidirectionally, may be detected. Any convenient flow detection protocol may be employed, including the approach shown in FIG. 5C where a check valve 55 is present at the flow outlet, where the valve allows for fluid outflow only.

Figure 6A:
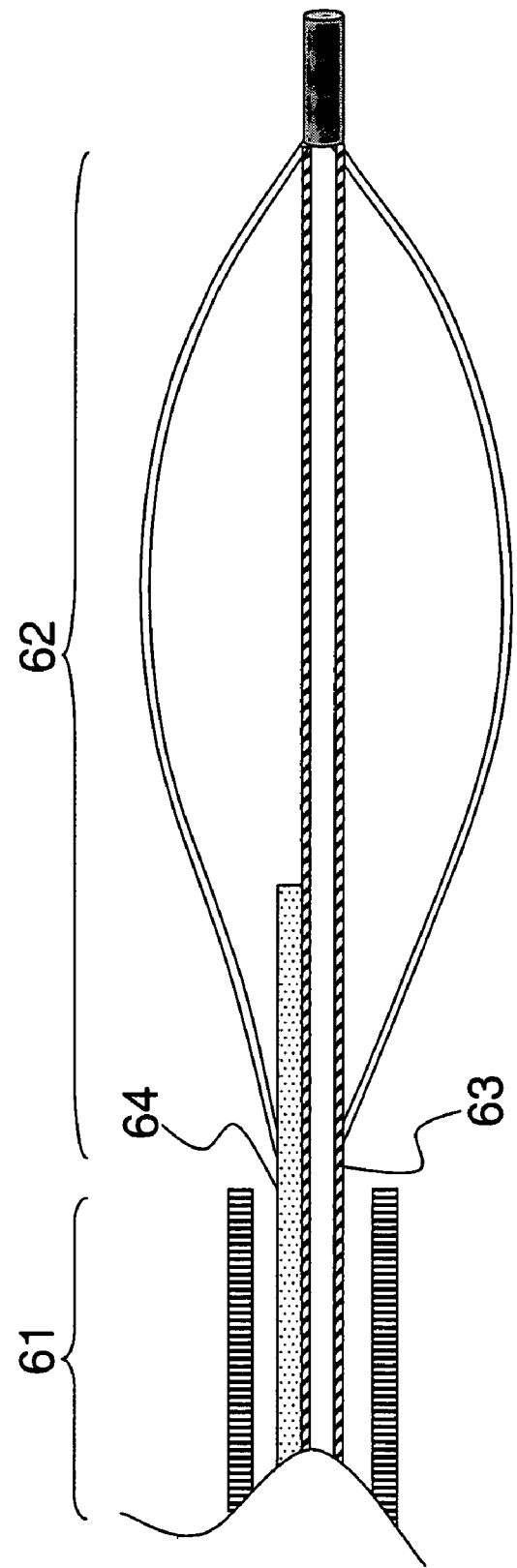
FIGS. 6A and 6B provide an illustration of another type of flow modulator that may be employed in certain embodiments of the invention.
Figure 6B:
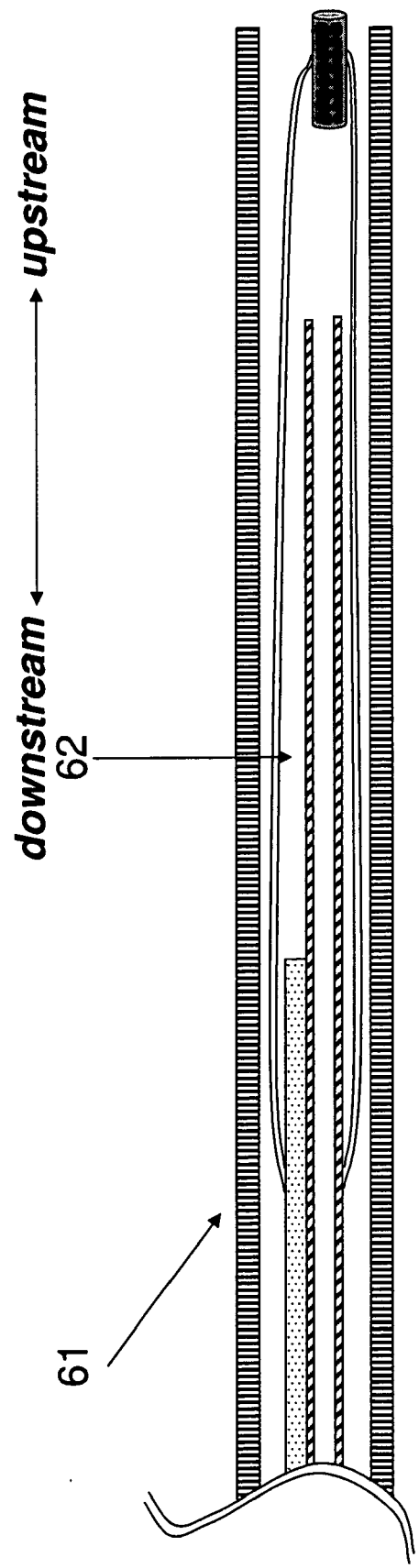

FIGS. 6A and 6B provide an illustration of another type of flow modulator that may be employed in certain embodiments of the invention. In FIGS. 6A and 6B, the flow modulator is non-flow through expandable flow modulator. A catheter 61 includes an expanding tip 62, which acts as a non-flow through flow modulator. The catheter 61 also incorporates an inner channel 63 for guide wire to facilitate over-the-wire (OTW) placement of the catheter 61. The catheter also incorporates at least one optical fiber 64 which terminates in the vicinity of the flow modulator. In one embodiment, at least one end of the expanding flow modulator 62 is axially movable against said inner channel 63. FIG. 6B provides a view of the device shown in FIG. 6A, where the flow modulator is collapsed and retracted into the lumen of the aspiration catheter, e.g., during placement of the catheter and/or when the catheter is not in use.

As summarized above, in certain embodiments, the methods may include a detection step, where a physiologic parameter and/or the agent and/or a physiological (e.g., anatomical) structure, etc., is detected in the efferent fluid collection site. Depending on the nature of the item to be detected, e.g., the physiologic parameter, the agent, etc., a variety of different types of sensors or detectors may be employed. Detectors of interest include, but are not limited to: fiber-optic based sensors, temperature sensors, acoustic sensors, pH detectors, capacitance-based detectors, fluid velocity detectors, conductivity detectors and detectors able to detect changes in ferroelectromagnetism or magnetic susceptibility (see e.g., Blood, 1 Jan. 2003, Vol. 101, No. 1, pp. 15-19) and the like. Detectors of interest include those detectors described in published United States Application Nos. 20050124969 and 20040254523, the disclosures of various detectors described therein are herein incorporated by reference.

The sensors or detectors may be associated with the aspiration device itself, e.g., be present on the flow modulator, the aspiration element, etc., or may be positioned in the efferent fluid collection site using a distinct or separate device.

Figure 7A:
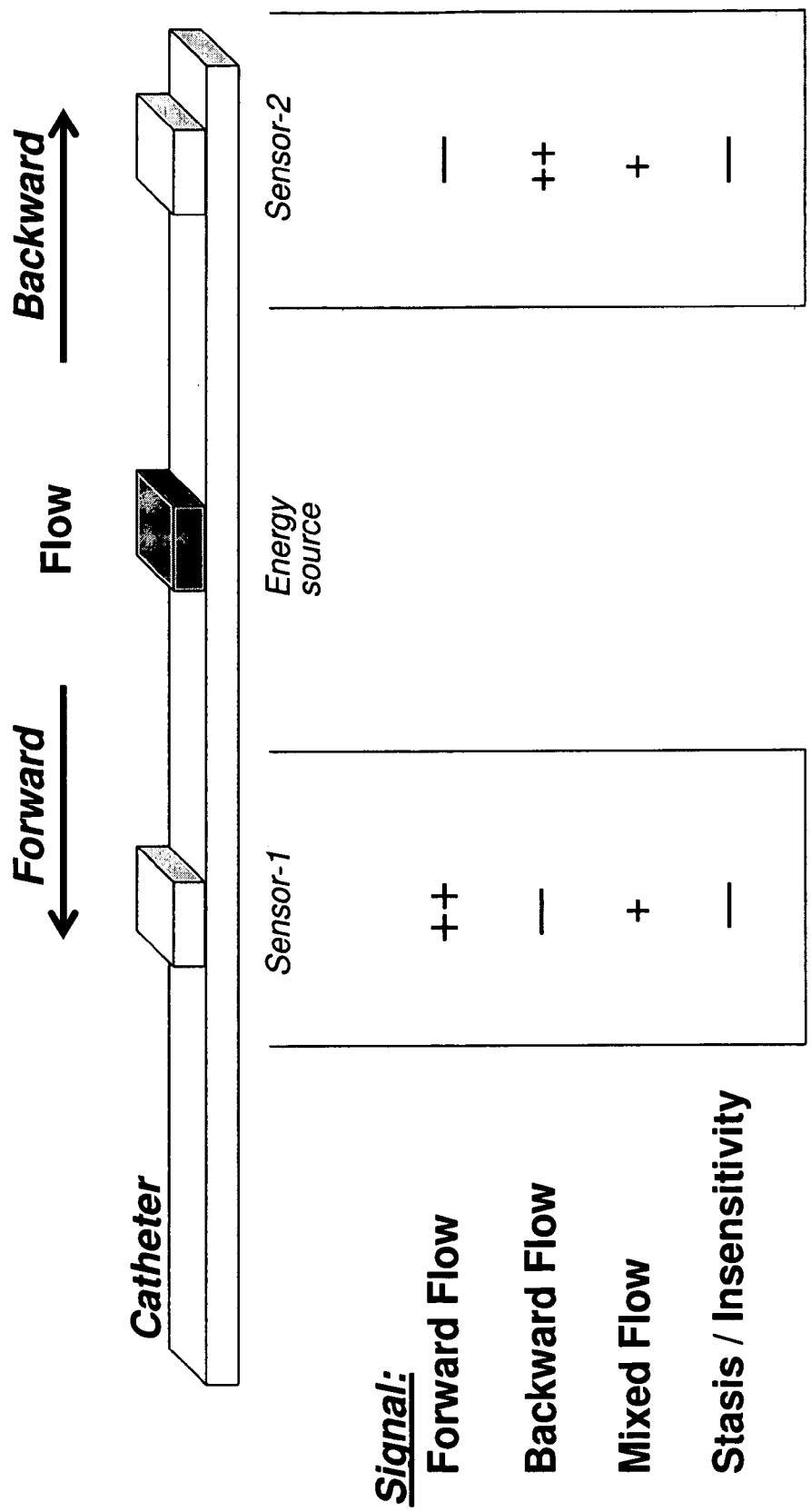

In certain embodiments, the methods include detection of fluid flow at the efferent fluid collection site. For such methods, any convenient flow detector may be employed. In certain embodiments, the flow detector is a hemodynamic sensor, which sensor is provided at the efferent fluid collection site. One type of a hemodynamic sensor is based on temperature, where a heating element can heat the fluid in first location and temperature sensors positioned at fixed locations upstream and downstream of the heating (or cooling element) element can detect changes in the temperature of the fluid medium flowing past them and from the detected changes determine direction of fluid flow. An embodiment of such a sensor is provided in FIG. 7A. Alternatively, the flow sensor could comprise a sensor material that is moved by fluid flow and generates signals in response to movement that can be employed to determine fluid flow. Such a sensor is depicted in FIG. 7B.

In certain embodiments, the detector is a detector configured to detect the presence of the agent to be removed in the efferent fluid collection site. As reviewed published United States Application Nos. 20050124969 and 20040254523, agents may be detected directly or indirectly. For example, an agent may be directly detected by detecting its optical or other properties. Alternatively, an agent may be indirectly detected by detecting changes that occur in response to presence of the agent in the efferent fluid collection site, e.g., changes in optical properties of the fluid, changes in physiology of the efferent fluid collection site, etc. In certain embodiments, a fiber optic detector is employed, which detects the presence of the agent, e.g., contrast agent, in the fluid when the agent is present at the efferent fluid collection site.

In certain embodiments, the detector is one that is associated with the aspiration device and, as such, is introduced into the efferent fluid collection site with the aspiration device. In some embodiments, the detector is introduced to the efferent fluid collection site through the aspiration element, where the detector is a fiber optic cable introduced through the aspiration element.

Figure 9:
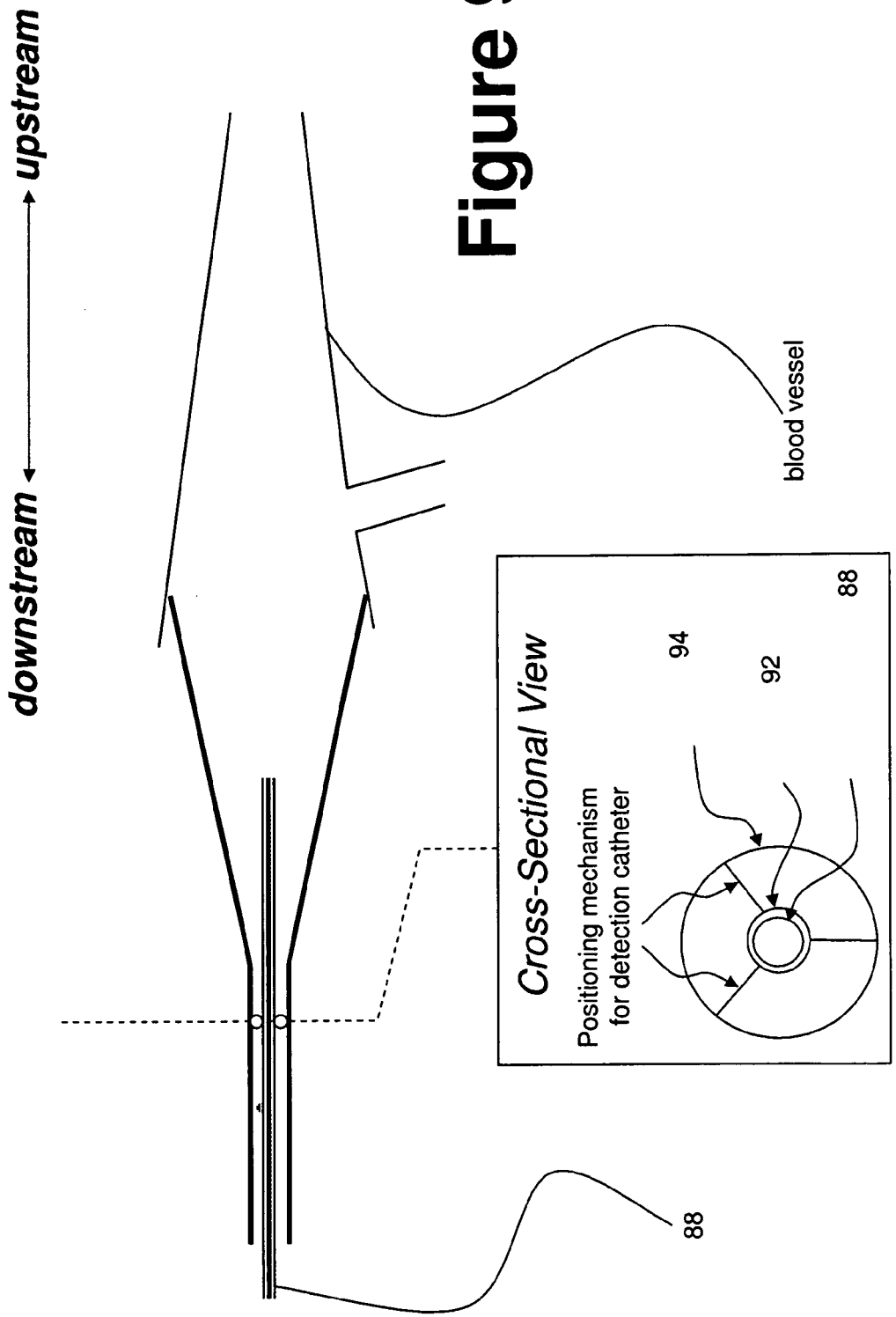
Figure 10:
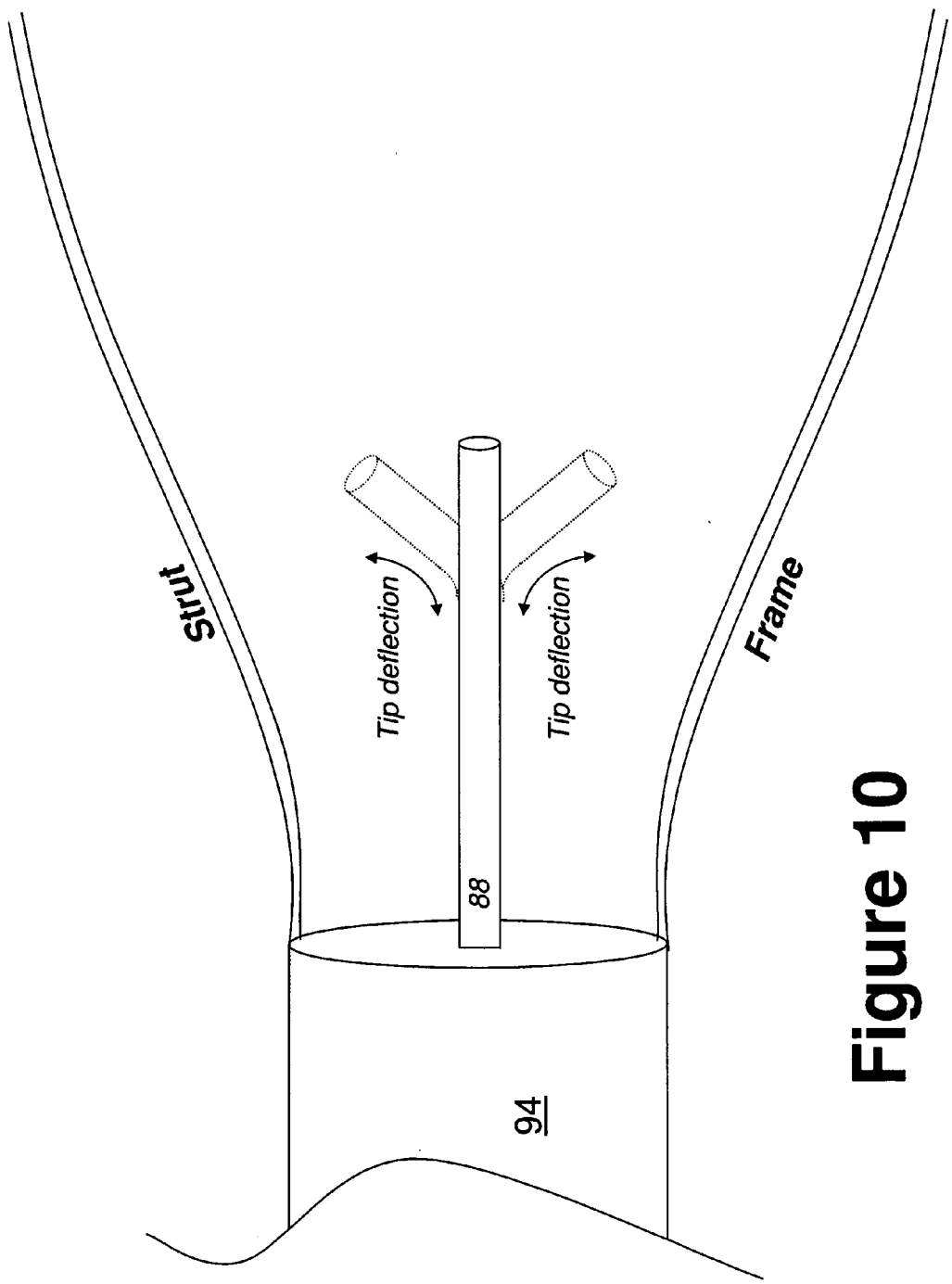

In certain embodiments, it is desirable to be able to precisely position the detector at a particular location in the efferent fluid collection site. Precise positioning of the detector in the target site can be accomplished using any convenient protocol. In certain embodiments, the aspiration device includes a centering mechanism that works to position the detector in the target site. An example of such a centering mechanism is shown in FIG. 8. In the device shown in FIG. 8, an articulation element 82 coupled to the wall of the flow modulator 84 by positioning mechanism 86 such that is positioned near the distal end of the detector catheter 88 serves to position the detector in the center of the flow modulator 84 at a desired location. An alternative embodiment is shown in FIG. 9. In the device shown in FIG. 9, an articulation element 92 coupled to the wall of the aspiration catheter 94 and positioned near the distal end of the aspiration catheter 94 serves to position the detector and detection catheter 88 in the center of the flow modulator at a desired location. In an alternative embodiment, the detector element is present on a steerable element, e.g., a steerable catheter, such that no distinct centering mechanism is required. Such an embodiment is shown in FIG. 10. Other embodiments of interest include those where the detector is incorporated into the wall of the aspiration element and embodiments where the detector is a separate element which can be closely associated with the device to provide for the desired placement, e.g., where it is configured to be passed through an outflow element of the device to be positioned in the desired location.

Systems

Also provided are systems for use in practicing the subject methods, where the systems include an aspiration device for selectively removing agent from the efferent fluid collection site, such as the representative devices described above, and may optionally include one or more additional components that find use in practicing the subject methods, e.g., detectors, agent introducers, data recorders, etc. In certain embodiments, the system includes an aspiration controller and aspiration mechanism operatively linked to an aspiration lumen which is introduced into the subject (body), as well as a number of additional/optional components, such as an injection/delivery system for introducing agent into the body at a site upstream of the target efferent fluid collection site, one or more detector elements for detecting the presence of agent in the efferent fluid collection site, and an aspiration recorder/display element for recording data (e.g., fluid flow data, etc.) and displaying the same to the operator. Of interest are the systems described in published United States Application Nos. 20050124969 and 20040254523, the disclosures of which systems described therein modified to include aspiration devices of the present invention are herein incorporated by reference.

Utility

The subject invention finds use in a wide variety of different applications, including both diagnostic and therapeutic applications. Of interest is the use of the subject methods and devices to selectively remove from a subject a locally administered diagnostic or therapeutic agent, so that the host or subject is not systemically exposed to the diagnostic or therapeutic agent.

In certain embodiments, the subject methods are employed to selectively remove a locally administered diagnostic agent, such that the diagnostic agent is only contacted with a limited region or portion of the host to which it is administered, e.g., a specific organ or portion thereof. A common example of such a compound is radio-opaque dye. Iodinated forms of such a dye are used routinely during catheter-based interventional procedures such as coronary, renal, neurological, angioplasty, and peripheral arteriography. The iodine component has a high absorption of x-rays and therefore provides a contrast medium for the radiological identification of vessels when introduced within an upstream artery. However, the use of such dyes is known to have potential toxic effects depending on the specific formulation, including direct injury to renal tubule cells, endothelial injury, bronchospasm, inflammatory reactions, pro-coagulation, anti-coagulation, vasodilation and thyrotoxicosis.

Another application of the subject invention is in the selective removal from a patient of a locally administered therapeutic agent, where representative therapeutic agents or materials that may be introduced locally for desired effects but whose direct or other effects would be undesired elsewhere include vasoactive agents, cytotoxic agents, genetic vectors, apoptotic agents, anoxic agents (including saline), photodynamic agents, emboli-promoting particles or coils, antibodies, cytokines, immunologically targeted agents and hormones. Additional agents of interest include, but are not limited to: cells, enzymes, activators, inhibitors and their precursors, as well as sclerosing agents, anti-inflammatories, pro-inflammatories, steroids and osmotic agents, and the like.

As such, another representative application of the subject methods is to determine the amount of agent retained at a local area or region of a subject upon local administration of the agent to the subject. For example, where a therapeutic agent is locally administered to a region or location of a subject, e.g., an organ, and blood carrying the agent is selectively removed from the subject according to the subject methods, the amount of agent in the collected blood can be used to determine the amount of agent that was retained by the local region or area, e.g., organ, of the subject. As such, in those cases where the present invention is used to retrieve a diagnostic or therapeutic agent for which a portion of that agent desirably resides in the region into which it is delivered, and the portion of the agent collected from the collection represents an amount of the agent that did not remain resident in that region, the subject methods may be employed to estimate the effective dosage of the agent. For example, in the localized delivery of a chemotherapeutic agent via the afferent branches of a targeted tumor, the present invention is capable of collecting some of the chemotherapeutic agent after it passes through tumor bed, but before it is able to enter into the systemic circulation, thus minimizing its side effects. The difference between the amount of agent injected and the amount of agent that is retrieved by the present invention represents the sum of the amount of agent that was successfully incorporated into the tumor and the amount of agent that escaped to the systemic circulation. If a goal of the localized delivery of the chemotherapeutic agent is to attempt to incorporate a given dosage of the agent into the tumor, it is possible to use the present invention to better estimate how much of the delivered agent was successfully incorporated into the tumor by estimating how much of the agent was retrieved in the collection site. Alternatively, the present invention can be used to allow higher dosage application of agent, the majority of which can then be detected and removed at efferent collection site of the target organ. If a higher than expected amount of agent was retrieved in the collection site, than a substantial portion of the agent was not successfully incorporated into the tumor and this may direct the physician to deliver more agent to the tumor, or consider alternative strategies for treatment. The higher the efficacy of the present invention is in terms of retrieving the agent, the more accurate the estimate of the amount of agent successfully delivered to the site will become.

Kits

Also provided are kits for use in practicing the subject methods, where the kits may include one or more of the above devices, and/or components of the subject systems, as described above. As such, a kit may include a device, such as a catheter device, that includes an aspiration lumen, aspiration mechanism and aspiration mechanism controller, as described above. The kit may further include other components, e.g., guidewires, etc., which may find use in practicing the subject methods.

In addition to above mentioned components, the subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The following example is offered by way of illustration, and not by way of limitation.

EXPERIMENTAL

I. Aim

The aim of the present experiment is to assess patterns of flow at the proximal coronary sinus in a glass model of the human heart. Specifically, the current experiment is designed to map the proximal coronary sinus in terms of flow paths of CS versus MCV.

II. Methods

For nomenclature purposes, CS segments upstream to MCV will be referred to as great cardiac vein (GCV). The flow from the GCV would naturally extend into and form the main CS flow (down-stream from MCV).

A glass model simulating the anatomy of the human heart was utilized to test the pattern of flow in the proximal CS. As a test medium, the glass heart model (GHM) was filled with sheep blood. A human-equivalent blood circulation was created utilizing a peristaltic flow pump at a flow rate of 2.3 L/min, leading to a realistic human CS flow of approximately 4 mL/sec.

For purposes of mapping flow paths of GCV, and MCV, a fiberoptic flow detector was used, which can be inserted into the proximal segments CS of GHM. Additionally, a method was developed to reliably position the detector at various positions inside the proximal CS to map flow paths of GCV and MCV.

When mapping the flow path of a specific tributary at a predetermined CS-position, radiographic contrast agent was injected into the tributary, and an input from the detector was registered. Absence of signal from the detector would indicate absence of agent's flow at the corresponding CS-position.

III. Summary of Result

Figure 11A:
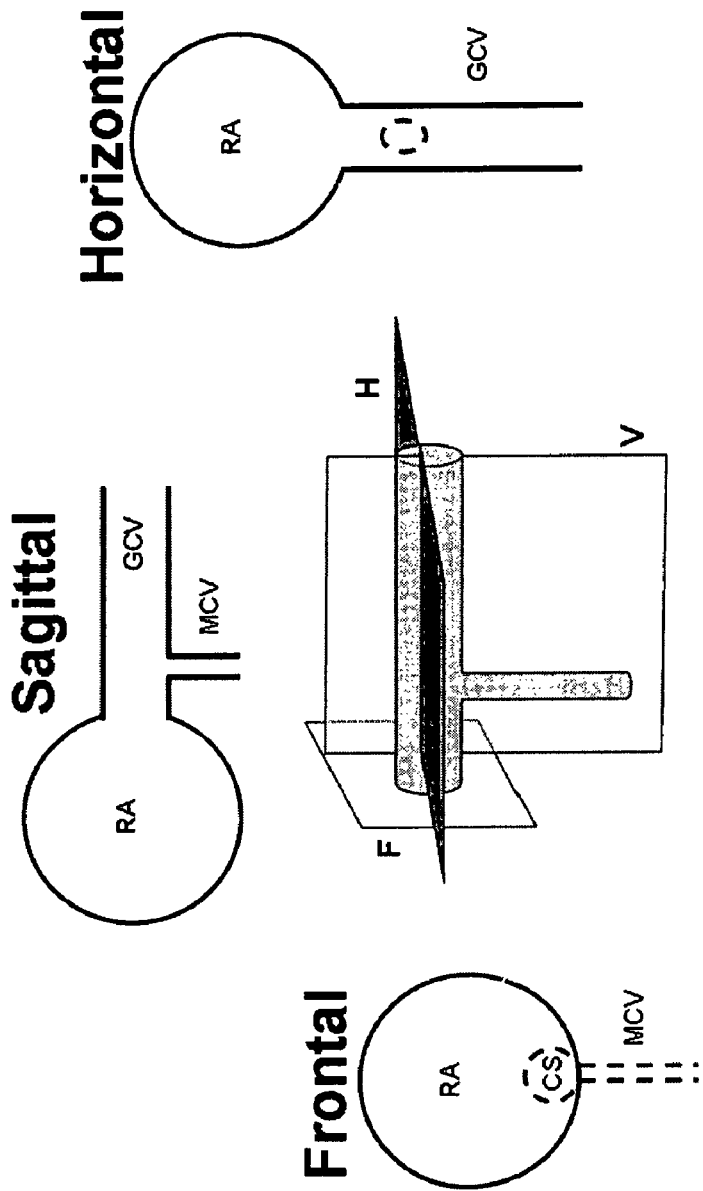

FIGS. 11A and 11B represent the CS of the GHM with its two main tributaries (MCV, and GCV). Also represented in FIGS. 11A and 11B are the testing positions of the detector. The detector was positioned in the proximal segment of the coronary sinus, specifically at or around the merging point of MCV, and proximal (=upstream) thereof.

Mapping flow of the GCV: Detection signals of GCV flow at various positions inside prox. CS revealed that GCV flow maintains an axial, straight flow toward the Os of CS, despite intersecting MCV flow.

Mapping flow of the MCV: Detection signal of the CS flow at various positions inside prox. CS revealed that MCV flow projects through GCV flow, and lands on the contralateral CS-wall. The MCV flow would then slows down, is deflected by the GCV/CS flow, and would flow eccentrically in axial direction toward the Os of CS.

D. Conclusion

At the proximal coronary sinus, flow mapping studies revealed that MCV flow intersects through (axial) GCV flow until it hits the contralateral wall of the CS.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for removing an agent from a physiological efferent fluid collection site of a living subject, said method comprising:
   introducing an aspiration device to a target site of said living subject at least proximal to said physiological efferent fluid collection site, wherein said aspiration device comprises an aspiration element and a flow modulator at a distal end of said aspiration element that is configured to converge intersecting fluid flow paths so that the flow paths are focused into said aspiration element, wherein said flow modulator comprises an expandable frame of two or more longitudinal elements and an impermeable membrane positioned between said two or more longitudinal elements and partially covering the expandable frame, said flow modulator being configured to produce an asymmetric fluid barrier that is radially asymmetric upon expansion of said expandable frame; and
   activating said aspiration device when said agent is at least predicted to be present in said target site to remove fluid comprising said agent from said subject;
   to selectively remove said agent from said physiological efferent fluid collection site.

2. The method according to claim 1, wherein said flow modulator is positioned at an intersection of two or more tributaries of said physiological efferent fluid collection site.

3. The method according to claim 2, wherein said method comprises expanding said frame at said intersection prior to activating said aspiration device.

4. The method according to claim 1, wherein said aspiration element and flow modulator are configured so that fluid flows past said aspiration element when said aspiration element is not activated.

5. The method according to claim 4, wherein said flow modulator comprises a flow outlet positioned downstream of said flow modulator.

6. The method according to claim 5, wherein said flow outlet is configured to allow bidirectional fluid flow.

7. The method according to claim 5, wherein said flow outlet is configured to allow unidirectional fluid flow.

8. The method according to claim 1, wherein said method further comprises detecting fluid flow in said efferent fluid collection site.

9. The method according to claim 8, wherein fluid flow is detected with a hemodynamic sensor.

10. The method according to claim 9, wherein said sensor is coupled to said flow modulator.

11. The method according to claim 1, wherein said method further comprises detecting said agent in said efferent fluid collection site with a detector.

12. The method according to claim 11, wherein said detector comprises a detection element that is introduced into said efferent fluid collection site through said aspiration element.

13. The method according to claim 12, wherein said method further comprises positioning said detector in said efferent fluid collection site with a positioning mechanism.

14. The method according to claim 13, wherein said positioning mechanism is operatively coupled to said flow modulator.

15. The method according to claim 13, wherein said positioning mechanism is operatively coupled to said detection catheter.

16. The method according to claim 1, wherein said physiological efferent fluid collection site is a vascular fluid collection site and said fluid is blood.

17. The method according to claim 16, wherein said vascular fluid collection site is a cardiovascular fluid collection site.

18. The method according to claim 17, wherein said cardiovascular fluid collection site is a coronary cardiovascular fluid collection site.

19. The method according to claim 18, wherein said coronary cardiovascular fluid collection site is a coronary sinus.

20. The method according to claim 1, wherein said physiological efferent fluid collection site is present in a mammal.

21. The method according to claim 20, wherein said mammal is a human.

22. The method according to claim 1, wherein said agent is a therapeutic agent.

23. The method according to claim 1, wherein said agent is a diagnostic agent.

24. The method according to claim 23, wherein said diagnostic agent is a contrast agent.

25. The method according to claim 1, wherein said method further comprises extracorporally separating agent from said fluid to produce an agent depleted fluid and then returning said agent depleted fluid to said body.

26. The method according to claim 1, wherein said method further comprises disposing of said fluid.

* * * * *